US008907055B2

(12) United States Patent
Kolatkar et al.

(10) Patent No.: US 8,907,055 B2
(45) Date of Patent: Dec. 9, 2014

(54) MUTANT SOX PROTEINS AND METHODS OF INDUCING PLURIPOTENCY

(75) Inventors: Prasanna R. Kolatkar, Singapore (SG); Irene Aksoy, Singapore (SG); Ralf Jauch, Singapore (SG); Lawrence W. Stanton, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/505,369

(22) PCT Filed: Nov. 4, 2010

(86) PCT No.: PCT/SG2010/000423
§ 371 (c)(1),
(2), (4) Date: May 1, 2012

(87) PCT Pub. No.: WO2011/056147
PCT Pub. Date: May 12, 2011

(65) Prior Publication Data
US 2012/0220029 A1    Aug. 30, 2012

Related U.S. Application Data

(60) Provisional application No. 61/272,793, filed on Nov. 4, 2009.

(51) Int. Cl.
*A61K 38/00* (2006.01)
*C07H 21/04* (2006.01)
*C12N 5/00* (2006.01)

(52) U.S. Cl.
USPC .......................... 530/326; 536/23.5; 435/377

(58) Field of Classification Search
USPC .......................... 530/326; 536/23.5; 435/377
See application file for complete search history.

(56) References Cited

U.S. PATENT DOCUMENTS

2007/0060743 A1* 3/2007 Tang et al. ................... 536/23.1

OTHER PUBLICATIONS

Office Action mailed Mar. 12, 2014 in corresponding European Patent Application No. 10828631.1.
International Search Report and Written Opinion issued Jan. 13, 2011 (issued in PCT Application No. PCT/SG2010/000423).
Response to written Opinion and Demand dated Sep. 5, 2011 (issued in PCT Application No. PCT/SG2010/000423).
International Preliminary Report on Patentability dated Oct. 7, 2011 (issued in PCT Application No. PCT/SG2010/000423).
Extended European Search Report dated May 17, 2013 issued corresponding application No. EP10828631.
Ambrosetti et al., "Synergistic Activation of the Fibroblast Growth Factor 4 Enhancer by Sox2 and Oct-3 Depends on Protein-Protein Interactions Facilitated by a Specific Spatial Arrangement of Factor Binding Sites", Molecular and Cellular Biology. Nov. 1997, vol. 12, pp. 6321-6329.
Avilion et al., "Multipotent cell lineages in early mouse development depend on SOX2 function", Genes & Development, Jan. 1, 2003, pp. 126-140, vol. 17, Issue 1.
Badis et al., "Diversity and Complexity in DNA Recognition by Transcription Factors", Science, Jun. 26, 2009, pp. 1720-1723, vol. 324, No. 5935.
Ben-Gal et al., "Identification of transcription factor binding sites wih variable-order Bayesian networks", Bioformatics, Jun. 1, 2005, pp. 2657-2666, vol. 21, Issue 11.
Bowels et al., "Phylogeny of the SOX Family of Developmental Transcription Factors Based on Sequence and Structural Indicators", Developmental Biology, Nov. 15, 2000, pp. 239-255, vol. 227, Issue 2.
Boyer et al., "Core Transcriptional Regulatory Circuitry in Human Embryonic Stem Cells", Cell, Sep. 23, 2005, pp.947-952, vol. 122, Issue 6.
Chien et al., "Inegration of exernal signaling pathways with the core transcriptional network in embryonic stem cells", Cell, Jun. 13, 2008, pp. 1106-1117, vol. 133, Issue 6.
Dailey et al., "Coevolution of HMG Domains and Homeodomains and the Generation of Tanscriptional Regulation by Sox/POU Complexes" Jounal of Cellualr Physiology 186:315-328 (2001).
EMBL database accession No.: BAE33732 (Sep. 7, 2005).
Hamanaka et al., Generation of germline-competent rat induced pluripotent stem cells, PLoS One, 2011;6(7):e22008. Epub Jul. 15, 2011.
Jauch et al., Conversion of Sox17 into a pluripotency reprogramming factor by reengineering its associatin with Oct4 on DNA. Stem Cells. Jun. 2011;29(6):940-51.
Jauch et al., "Crystal Structure and DNA Binding of the Homeodomain of the Stem Cell Transcription Factor Nanog", Journal of Molecular Biology, Feb. 22, 2008, pp. 758-770, vol. 376, Issue 3.
Kamachi et al., "Mechanism of Regulatory Target Selection by the SOX High-Mobility-Group Domain Proteins as Revealed by the Comparison of SOX 1/2/3 and SOX9", Molecular and Cellular Biology, Jan. 1999, pp.107-120, vol. 19, Issue 1.
Kanai-Azuma et al., Depletion of definitive gut endoderm in Sox17-null mutant mice. Development, May 2002, pp. 2367-2379, vol. 129, Issue 10.
Kim et al., "An extended transcriptional network for pluripotency of embryonic stem cells" Cell. Mar. 21, 2008; 132(6). 24 pages.
Kuhlbrodt et al., "Cooperative Function of POU Proteins and SOX Proteins in Glial Cells", The Journal of Biological Chemistry, Jun. 26, 1998, pp. 16050-16057, vol. 273, Issue 26.

(Continued)

*Primary Examiner* — Marcia S Noble
(74) *Attorney, Agent, or Firm* — Wolf, Greenfield & Sacks, P.C.

(57) ABSTRACT

There is presently provided mutant Sox2, Sox7 and Sox17 proteins that have acquired or increased ability to induce pluripotency in a partially differentiated or fully differentiated cell. Sox7 and Sox17 are mutated to resemble in part Sox2, or Sox2 is mutated to resemble in part Sox7 or Sox17. In one aspect, the Oct4 contact interface of Sox7 or Sox17 is mutated. In another aspect, the high mobility group (HMG) of Sox2 is fused to the C-terminal activation domain of Sox7 or Sox17. Methods relating to inducing pluripotency using a mutant Sox2, Sox7 or Sox17 protein are also provided.

10 Claims, 22 Drawing Sheets

(56) References Cited

OTHER PUBLICATIONS

Kurimoto et al., "An improved single-cell cDNA amplification method for efficient high-density oligonucleotide microarray analysis", Nucleic Acids Res. Mar. 17, 2006; 34(5):e42. Print 2006.

Ledebvre et al., "Control of Cell Fate and Differentiation by Sry-related High-mobility-group Box (Sox) Transcription Factors", Int J Biochem Cell Biol. 2007 ; 39(12): 219-2214.

Loh et al., "The Oct4 and Nanog transcription network regulates pluripotency in mouse embryonic stem cells", Nature Genetics, Apr. 2006, pp. 431-440, vol. 38, Issue 4.

Magie et al., "Genomic inventory and expression of SOX and FOX genes in the cnidarian Nematostella vectensis", Development Genes and Evolution, Springer, Berlin, Germany, Dec. 1, 2005, pp. 618-630, vol. 215, No. 12.

Nakagawa et al., "Generation of induced pluripotent stem cells wihtout Myc from mouse and human fibroblasts", Nature Biotechnology, Jan. 2008, pp. 101-106, vol. 26, Issue 1.

Ng et al., "Purification, crystallization and preliminary X-ray diffraction analysis of the HMG domain of Sox17 in complex with DNA," Acta Crystallographica Section F, Structural Biology and Crystallization Communications. F64, 1184-1187.

Nicholas et al., "Formation of the Pluripoint Stem Cells in the Mammalian Embryo Depends on the POU Transcription Factor Oct4", Cell, Oct. 30, 1998, pp.379-391, vol. 95, Issue 3.

Nowling et al., "Identification of the Transactivation Domain of the Transcription Factor Sox-2 and an Associated Co-activator", The Journal of Biological Chemistry, vol. 275, No. 6, Issue of Feb. 11, pp. 3818-2000.

Okita et al., "Generation of Mouse Induced Pluripoint Stem Cells Without Viral Vectors", Science, Nov. 7, 2008, pp. 949-953, vol. 322, No. 5903.

Okita et al., "Generation of the germline-competent induced pluripoint stem cells", Nature, Jul. 19, 2007, pp. 313-317, vol. 448, No. 7151.

Okubo et al. "Sox2 is required for development of taste bud sensory cells", Genes & Development, Oct. 1, 2006, pp. 2654-2659, vol. 20, Issue 19.

Palasingam et al., The structure of Sox17 Bound to DNA Reveals a Conversed Bending Topology but Selective Protein Interaction Platforms. Journal of Molecular Biology, May 8, 2009, pp. 619-630, vol. 388, Issue 3.

Que et al., "Multiple dose-dependant roles for Sox2 in the patterning and differentiation of anterior foregut endoderm", Development, Jul. 2007, pp. 2521-2531, vol. 134, Issue 13.

Que et al., "Multiple roles for Sox2 in the developing and adult mouse trachea", Development, Jun. 2009, pp. 1899-1907, vol. 136, Issue 11.

Reim et al., "The POU Domain Protein Spg (Pou2/Oct4) Is Essential for Endoderm Formation in Cooperation with the HMG Domain Protein Casnova", Developmental Cell, Jan. 2004, pp. 91-101, vol. 6, Issue 1.

Remenyi et al., "Crystal structure of a POU/HMG/DNA ternary complex suggests differential assembly of Oct4 and Sox2 on two enhancers", Genes & Developmet, Aug. 15, 2003, pp. 2048-2059, vol. 17, Issue 16.

Rodda et al., "Transcriptional Regulation of Nanog by OCT4 and SOX2", The Journal of Biological Chemistry, Jul. 1, 2005, pp. 24731-24737, vol. 280, Issue 26.

Ryan et al., "POU domain family values: flexibility, partnerships, and developmental codes", Genes & Development, May 15, 1997, pp. 1207-1225, vol. 11, Issue 10.

Scaffidi et al., "Spatially Precise DNA Bending is and Essential Activity of the Sox2 Transcription Factor", The Journal of Biological Chemistry, Dec. 14, 2001, pp. 47296-47302, vol. 276, Issue 50.

Segal et al., "What controls nucleosome positions?", Trends in Genetics, Aug. 2009, pp. 335-343, vol. 25, Issue 8.

Seguin et al., "Establishment of Endoderm Progenitors by SOX Transcription Factor Expression in Human Embryonic Stem Cells", Cell Stem Cell, Aug. 7, 2008. pp. 182-195, vol. 3, Issue 2.

Shimoda et al., "Sox17 plays a substantial role in late-stage differentiation of the extraembryonic endoderm in vitro", Journal of Cell Science, Nov. 1, 2007, pp. 3859-3869, vol. 120, Issue 21.

Stefanovic et al., "Interplay of Oct4 with the Sox17: a molecular switch from stem cell pluripotency to specifying a cardiac fate", The Journal of Cell Biology, Sep. 7, 2009, pp. 665-673, vol. 186, Issue 5.

Sun et al., "Feeder-free derivation of induced pluripotent stem cells from adult human adipose stem cells", Proceedings of the National Academy of Sciences of the United States of America, Sep. 15, 2009, pp. 15720-15725, vol. 106, Issue 37.

Takahashi et al., "Induction of pluripotent stem cells form mouse embryonic and adult fibroblasts cultures by defined factors", Cell, Aug. 25, 2006, pp. 663-676. vol. 126, Issue 4.

Tanka et al., "Interplay of SOX and PUO Factors in regulation of the Nestin Gene in Neural Primordial Cells", Molecular and Cellualr Biology, Oct. 2004, pp. 8834-8846, vol. 24, Issue 20.

Tsuda et al., "Transcriptional Co-activators CREB-binding Protein and p300 Regualte Chondrocyte-specific Gene Expression via Association with Sox9", May 5, 2003 The Journal of Biological Chemistry, 278, 27224-27229.

Van Loo et al., "Computational methods for the detection of the cis-regulatory modules", Briefings in Bioinformatics, 2009, pp. 509-524, vol. 10, Issue 5.

Wegner, "From head to toes: the multiple facets of Sox proteins", Nucleic Acid Research, Mar. 1999, pp. 1409-1420, vol. 27, Issue 6.

Wernig, "In vitro reprogramming of fibroblasts into a pluripotent ES-cell-like state", Nature, Jul. 19, 2007, pp. 318-325, vol. 448, No. 7151.

Williams et al., "Molecular Basis for Synergistic Transcriptional Activation by Oct1 and Sox2 Revealed from the Solution Structure of the 42-kDa Oct1•Sox2•Hoxb 1-DNA Ternary Transcription Factor Complex", The Journal of Biological Chemistry, Jan. 9, 2004, pp. 1449-1457, vol. 279, Issue 2.

Wilson et al., "Matching SOX: partner proteins and co-factors of the SOX family of transcriptional regulators", Current Opinion in Genetics & Development, Aug. 2002, pp. 441-446, vol. 12, Issue 4.

Yuan et al.,"Developmental-Specific activity of the FGF-4 enhancer requires the synergistic action of the Sox2 and the Oct-3" Genes Dev. 1995 9: 2635-2645.

Zappone et al., "Sox2 reguatltory sequences direct expression of a β-geo transgene to telencephalic neural stem cells and precursors of the mouse embryo, revealing regionalization of the gene expression in CNS stem cells", Development, Jun. 2000, pp. 2367-2382, vol. 127, Issue 11.

* cited by examiner

SEQUENCE LISTING

```
<160> NUMBER OF SEQ ID NOS: 53

<210> SEQ ID NO 1
<211> LENGTH: 23
<212> TYPE: DNA
<213> ORGANISM: artificial
<220> FEATURE:
<223> OTHER INFORMATION: synthetic primer

<400> SEQUENCE: 1
caccatgggc ggcaaccaga aga                                         23

<210> SEQ ID NO 2
<211> LENGTH: 30
<212> TYPE: DNA
<213> ORGANISM: artificial
<220> FEATURE:
<223> OTHER INFORMATION: synthetic primer

<400> SEQUENCE: 2
ttacatgctg ttcccgccgg gggccagcaa                                  30

<210> SEQ ID NO 3
<211> LENGTH: 20
<212> TYPE: DNA
<213> ORGANISM: artificial
<220> FEATURE:
<223> OTHER INFORMATION: synthetic primer

<400> SEQUENCE: 3
cacccccgag gagtcccagg                                             20

<210> SEQ ID NO 4
<211> LENGTH: 25
<212> TYPE: DNA
<213> ORGANISM: artificial
<220> FEATURE:
<223> OTHER INFORMATION: synthetic primer

<400> SEQUENCE: 4
tcattctcgt tgggaatact caata                                       25

<210> SEQ ID NO 5
<211> LENGTH: 58
<212> TYPE: DNA
<213> ORGANISM: artificial
<220> FEATURE:
<223> OTHER INFORMATION: synthetic primer

<400> SEQUENCE: 5
ggggacaagt ttgtacaaaa aagcaggctt caccatgtat aacatgatgg agacggag   58

<210> SEQ ID NO 6
<211> LENGTH: 50
<212> TYPE: DNA
<213> ORGANISM: artificial
```

```
<220> FEATURE:
<223> OTHER INFORMATION: synthetic primer

<400> SEQUENCE: 6
ggggaccact ttgtacaaga aagctgggtt cacatgtgcg acagggcag        50

<210> SEQ ID NO 7
<211> LENGTH: 51
<212> TYPE: DNA
<213> ORGANISM: artificial
<220> FEATURE:
<223> OTHER INFORMATION: synthetic primer

<400> SEQUENCE: 7
ggggacaagt ttgtacaaaa aagcaggctt caccatgagc agcccggatg c      51

<210> SEQ ID NO 8
<211> LENGTH: 49
<212> TYPE: DNA
<213> ORGANISM: artificial
<220> FEATURE:
<223> OTHER INFORMATION: synthetic primer

<400> SEQUENCE: 8
ggggaccact ttgtacaaga aagctgggtt taaatgtcgg ggtagttgc        49

<210> SEQ ID NO 9
<211> LENGTH: 31
<212> TYPE: DNA
<213> ORGANISM: artificial
<220> FEATURE:
<223> OTHER INFORMATION: synthetic primer

<400> SEQUENCE: 9
catcgacgag gccgagcggc tgcgcgctct g                           31

<210> SEQ ID NO 10
<211> LENGTH: 78
<212> TYPE: DNA
<213> ORGANISM: artificial
<220> FEATURE:
<223> OTHER INFORMATION: synthetic primer

<400> SEQUENCE: 10
gagaagcggc cgttcgtcga ggaggccgag cggctgcgcg ttcagcacat gcaggaccac    60
ccgaattata aataccgg                                                 78

<210> SEQ ID NO 11
<211> LENGTH: 30
<212> TYPE: DNA
<213> ORGANISM: artificial
<220> FEATURE:
<223> OTHER INFORMATION: synthetic primer

<400> SEQUENCE: 11
gtggaagagg ccaagcggct gcgcgtgcag                            30

<210> SEQ ID NO 12
<211> LENGTH: 21
<212> TYPE: DNA
<213> ORGANISM: artificial
<220> FEATURE:
<223> OTHER INFORMATION: synthetic primer

<400> SEQUENCE: 12
```
gggtggacca tcctctagac t                                             21

<210> SEQ ID NO 13
<211> LENGTH: 20
<212> TYPE: DNA
<213> ORGANISM: artificial
<220> FEATURE:
<223> OTHER INFORMATION: synthetic primer

<400> SEQUENCE: 13
tcaaatgtcg gggtagttgc                                               20

<210> SEQ ID NO 14
<211> LENGTH: 18
<212> TYPE: DNA
<213> ORGANISM: artificial
<220> FEATURE:
<223> OTHER INFORMATION: synthetic primer

<400> SEQUENCE: 14
gggcagtgtg ccgttaat                                                 18

<210> SEQ ID NO 15
<211> LENGTH: 20
<212> TYPE: DNA
<213> ORGANISM: artificial
<220> FEATURE:
<223> OTHER INFORMATION: synthetic primer

<400> SEQUENCE: 15
aaggccctgt cacacttctg                                               20

<210> SEQ ID NO 16
<211> LENGTH: 20
<212> TYPE: DNA
<213> ORGANISM: artificial
<220> FEATURE:
<223> OTHER INFORMATION: synthetic primer

<400> SEQUENCE: 16
cagtttgaat gcatgggaga                                               20

<210> SEQ ID NO 17
<211> LENGTH: 20
<212> TYPE: DNA
<213> ORGANISM: artificial
<220> FEATURE:
<223> OTHER INFORMATION: synthetic primer

<400> SEQUENCE: 17
tgttctcgtc gtttcctcaa                                               20

<210> SEQ ID NO 18
<211> LENGTH: 30
<212> TYPE: DNA
<213> ORGANISM: artificial
<220> FEATURE:
<223> OTHER INFORMATION: synthetic primer

<400> SEQUENCE: 18
cggcgcggca ttgtatgcaa atcggcggcg                                    30

<210> SEQ ID NO 19
<211> LENGTH: 30
<212> TYPE: DNA
<213> ORGANISM: artificial

```
<220> FEATURE:
<223> OTHER INFORMATION: synthetic primer

<400> SEQUENCE: 19
ggcgcggcat tgtcatgcaa atcggcggcg                                   30

<210> SEQ ID NO 20
<211> LENGTH: 30
<212> TYPE: DNA
<213> ORGANISM: artificial
<220> FEATURE:
<223> OTHER INFORMATION: synthetic primer

<400> SEQUENCE: 20
ggcgcggcat tgtcgatgca aatcggcggc                                   30

<210> SEQ ID NO 21
<211> LENGTH: 30
<212> TYPE: DNA
<213> ORGANISM: artificial
<220> FEATURE:
<223> OTHER INFORMATION: synthetic primer

<400> SEQUENCE: 21
gcgcggcatt gtcggatgca aatcggcggc                                   30

<210> SEQ ID NO 22
<211> LENGTH: 30
<212> TYPE: DNA
<213> ORGANISM: artificial
<220> FEATURE:
<223> OTHER INFORMATION: synthetic primer

<400> SEQUENCE: 22
gcgcggcatt gtcggcatgc aaatcggcgg                                   30

<210> SEQ ID NO 23
<211> LENGTH: 30
<212> TYPE: DNA
<213> ORGANISM: artificial
<220> FEATURE:
<223> OTHER INFORMATION: synthetic primer

<400> SEQUENCE: 23
cgcggcattg tcgggcatgc aaatcggcgg                                   30

<210> SEQ ID NO 24
<211> LENGTH: 30
<212> TYPE: DNA
<213> ORGANISM: artificial
<220> FEATURE:
<223> OTHER INFORMATION: synthetic primer

<400> SEQUENCE: 24
cgcggcattg tcgggcgatg caaatcggcg                                   30

<210> SEQ ID NO 25
<211> LENGTH: 30
<212> TYPE: DNA
<213> ORGANISM: artificial
<220> FEATURE:
<223> OTHER INFORMATION: synthetic primer

<400> SEQUENCE: 25
gcggcattgt ccgggcgatg caaatcggcg                                   30
```

<210> SEQ ID NO 26
<211> LENGTH: 30
<212> TYPE: DNA
<213> ORGANISM: artificial
<220> FEATURE:
<223> OTHER INFORMATION: synthetic primer

<400> SEQUENCE: 26
gcggcattgt ccgggcggat gcaaatcggc                                    30

<210> SEQ ID NO 27
<211> LENGTH: 30
<212> TYPE: DNA
<213> ORGANISM: artificial
<220> FEATURE:
<223> OTHER INFORMATION: synthetic primer

<400> SEQUENCE: 27
cggcattgtc gcgggcggat gcaaatcggc                                    30

<210> SEQ ID NO 28
<211> LENGTH: 30
<212> TYPE: DNA
<213> ORGANISM: artificial
<220> FEATURE:
<223> OTHER INFORMATION: synthetic primer

<400> SEQUENCE: 28
cggcattgtc gcgggcggca tgcaaatcgg                                    30

<210> SEQ ID NO 29
<211> LENGTH: 30
<212> TYPE: DNA
<213> ORGANISM: artificial
<220> FEATURE:
<223> OTHER INFORMATION: synthetic primer

<400> SEQUENCE: 29
ggcattgtcc gcgggcggca tgcaaatcgg                                    30

<210> SEQ ID NO 30
<211> LENGTH: 30
<212> TYPE: DNA
<213> ORGANISM: artificial
<220> FEATURE:
<223> OTHER INFORMATION: synthetic primer

<400> SEQUENCE: 30
ggcgcggatg caaatcattg tccggcggcg                                    30

<210> SEQ ID NO 31
<211> LENGTH: 30
<212> TYPE: DNA
<213> ORGANISM: artificial
<220> FEATURE:
<223> OTHER INFORMATION: synthetic primer

<400> SEQUENCE: 31
ggcgcggcat tgtcatttgc atcggcggcg                                    30

<210> SEQ ID NO 32
<211> LENGTH: 30
<212> TYPE: DNA
<213> ORGANISM: artificial
<220> FEATURE:
<223> OTHER INFORMATION: synthetic primer

```
<400> SEQUENCE: 32
ggcgcgggac aatgatgcaa atcggcggcg                                          30

<210> SEQ ID NO 33
<211> LENGTH: 30
<212> TYPE: DNA
<213> ORGANISM: artificial
<220> FEATURE:
<223> OTHER INFORMATION: synthetic primer

<400> SEQUENCE: 33
gcggcattgt ccattgtcat gcaaatcggc                                          30

<210> SEQ ID NO 34
<211> LENGTH: 28
<212> TYPE: DNA
<213> ORGANISM: artificial
<220> FEATURE:
<223> OTHER INFORMATION: synthetic primer

<400> SEQUENCE: 34
catggacatt gtaatgcaaa agaagctg                                            28

<210> SEQ ID NO 35
<211> LENGTH: 22
<212> TYPE: DNA
<213> ORGANISM: artificial
<220> FEATURE:
<223> OTHER INFORMATION: synthetic primer

<400> SEQUENCE: 35
ctggacattg tatgcaaaag aa                                                  22

<210> SEQ ID NO 36
<211> LENGTH: 21
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(21)
<223> OTHER INFORMATION: Oct4 contact interface from Sox7

<400> SEQUENCE: 36

Leu Ser Gln Lys Arg Pro Tyr Val Asp Glu Ala Glu Arg Leu Arg Leu
1               5                   10                  15

Gln His Met Gln Asp
            20

<210> SEQ ID NO 37
<211> LENGTH: 21
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(21)
<223> OTHER INFORMATION: Oct4 contact interface from Sox17

<400> SEQUENCE: 37

Leu Ala Glu Lys Arg Pro Phe Val Glu Glu Ala Glu Arg Leu Arg Val
1               5                   10                  15

Gln His Met Gln Asp
```

<210> SEQ ID NO 38
<211> LENGTH: 319
<212> TYPE: PRT
<213> ORGANISM: Mus musculus
<220> FEATURE:
<221> NAME/KEY: MISC_FEATURE
<223> OTHER INFORMATION: Sox2

<400> SEQUENCE: 38

| | | | | | | | | | | | | | | |
|---|---|---|---|---|---|---|---|---|---|---|---|---|---|---|
| Met | Tyr | Asn | Met | Met | Glu | Thr | Glu | Leu | Lys | Pro | Pro | Gly | Pro | Gln | Gln |
| 1 | | | | 5 | | | | | 10 | | | | | 15 | |
| Ala | Ser | Gly | Gly | Gly | Gly | Gly | Gly | Asn | Ala | Thr | Ala | Ala | Ala | Thr |
| | | | 20 | | | | | 25 | | | | | 30 | |
| Gly | Gly | Asn | Gln | Lys | Asn | Ser | Pro | Asp | Arg | Val | Lys | Arg | Pro | Met | Asn |
| | | | 35 | | | | 40 | | | | | 45 | | | |
| Ala | Phe | Met | Val | Trp | Ser | Arg | Gly | Gln | Arg | Arg | Lys | Met | Ala | Gln | Glu |
| | 50 | | | | | 55 | | | | | 60 | | | | |
| Asn | Pro | Lys | Met | His | Asn | Ser | Glu | Ile | Ser | Lys | Arg | Leu | Gly | Ala | Glu |
| 65 | | | | | 70 | | | | | 75 | | | | | 80 |
| Trp | Lys | Leu | Leu | Ser | Glu | Thr | Glu | Lys | Arg | Pro | Phe | Ile | Asp | Glu | Ala |
| | | | | 85 | | | | | 90 | | | | | 95 | |
| Lys | Arg | Leu | Arg | Ala | Leu | His | Met | Lys | Glu | His | Pro | Asp | Tyr | Lys | Tyr |
| | | | 100 | | | | | 105 | | | | | 110 | | |
| Arg | Pro | Arg | Arg | Lys | Thr | Lys | Thr | Leu | Met | Lys | Lys | Asp | Lys | Tyr | Thr |
| | | 115 | | | | | 120 | | | | | 125 | | | |
| Leu | Pro | Gly | Gly | Leu | Leu | Ala | Pro | Gly | Gly | Asn | Ser | Met | Ala | Ser | Gly |
| | 130 | | | | | 135 | | | | | 140 | | | | |
| Val | Gly | Val | Gly | Ala | Gly | Leu | Gly | Ala | Gly | Val | Asn | Gln | Arg | Met | Asp |
| 145 | | | | | 150 | | | | | 155 | | | | | 160 |
| Ser | Tyr | Ala | His | Met | Asn | Gly | Trp | Ser | Asn | Gly | Ser | Tyr | Ser | Met | Met |
| | | | | 165 | | | | | 170 | | | | | 175 | |
| Gln | Glu | Gln | Leu | Gly | Tyr | Pro | Gln | His | Pro | Gly | Leu | Asn | Ala | His | Gly |
| | | | 180 | | | | | 185 | | | | | 190 | | |
| Ala | Ala | Gln | Met | Gln | Pro | Met | His | Arg | Tyr | Asp | Val | Ser | Ala | Leu | Gln |
| | | | 195 | | | | | 200 | | | | | 205 | | |
| Tyr | Asn | Ser | Met | Thr | Ser | Ser | Gln | Thr | Tyr | Met | Asn | Gly | Ser | Pro | Thr |
| | 210 | | | | | 215 | | | | | 220 | | | | |
| Tyr | Ser | Met | Ser | Tyr | Ser | Gln | Gln | Gly | Thr | Pro | Gly | Met | Ala | Leu | Gly |
| 225 | | | | | 230 | | | | | 235 | | | | | 240 |
| Ser | Met | Gly | Ser | Val | Val | Lys | Ser | Glu | Ala | Ser | Ser | Ser | Pro | Pro | Val |
| | | | | 245 | | | | | 250 | | | | | 255 | |
| Val | Thr | Ser | Ser | Ser | His | Ser | Arg | Ala | Pro | Cys | Gln | Ala | Gly | Asp | Leu |
| | | | 260 | | | | | 265 | | | | | 270 | | |
| Arg | Asp | Met | Ile | Ser | Met | Tyr | Leu | Pro | Gly | Ala | Glu | Val | Pro | Glu | Pro |
| | | 275 | | | | | 280 | | | | | 285 | | | |
| Ala | Ala | Pro | Ser | Arg | Leu | His | Met | Ala | Gln | His | Tyr | Gln | Ser | Gly | Pro |
| | 290 | | | | | 295 | | | | | 300 | | | | |
| Val | Pro | Gly | Thr | Ala | Ile | Asn | Gly | Thr | Leu | Pro | Leu | Ser | His | Met |
| 305 | | | | | 310 | | | | | 315 | | | | | |

<210> SEQ ID NO 39
<211> LENGTH: 317
<212> TYPE: PRT
<213> ORGANISM: Homo sapiens
<220> FEATURE:

<221> NAME/KEY: MISC_FEATURE
<223> OTHER INFORMATION: Sox2

<400> SEQUENCE: 39

Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315

<210> SEQ ID NO 40
<211> LENGTH: 380
<212> TYPE: PRT
<213> ORGANISM: Mus musculus
<220> FEATURE:
<221> NAME/KEY: MISC_FEATURE
<223> OTHER INFORMATION: Sox7

<400> SEQUENCE: 40

Met Ala Ser Leu Leu Gly Ala Tyr Pro Trp Thr Glu Gly Leu Glu Cys
1               5                   10                  15

Pro Ala Leu Glu Ala Glu Leu Ser Asp Gly Leu Ser Pro Pro Ala Val
            20                  25                  30

Pro Arg Pro Ser Gly Asp Lys Ser Glu Ser Arg Ile Arg Arg Pro
        35                  40                  45

Met Asn Ala Phe Met Val Trp Ala Lys Asp Glu Arg Lys Arg Leu Ala
 50                  55                  60

Val Gln Asn Pro Asp Leu His Asn Ala Glu Leu Ser Lys Met Leu Gly
65                  70                  75                  80

Lys Ser Trp Lys Ala Leu Thr Leu Ser Gln Lys Arg Pro Tyr Val Asp
                85                  90                  95

Glu Ala Glu Arg Leu Arg Leu Gln His Met Gln Asp Tyr Pro Asn Tyr
            100                 105                 110

Lys Tyr Arg Pro Arg Arg Lys Lys Gln Gly Lys Arg Leu Cys Lys Arg
            115                 120                 125

Val Asp Pro Gly Phe Leu Leu Ser Ser Leu Ser Arg Asp Gln Asn Thr
            130                 135                 140

Leu Pro Glu Lys Asn Gly Ile Gly Arg Gly Glu Lys Glu Asp Arg Gly
145                 150                 155                 160

Glu Tyr Ser Pro Gly Ala Thr Leu Pro Gly Leu His Ser Cys Tyr Arg
                165                 170                 175

Glu Gly Ala Ala Ala Pro Gly Ser Val Asp Thr Tyr Pro Tyr Gly
            180                 185                 190

Leu Pro Thr Pro Pro Glu Met Ser Pro Leu Asp Ala Leu Glu Pro Glu
                195                 200                 205

Gln Thr Phe Phe Ser Ser Cys Gln Glu His Gly His Pro His
    210                 215                 220

His Leu Pro His Leu Pro Gly Pro Pro Tyr Ser Pro Glu Phe Thr Pro
225                 230                 235                 240

Ser Pro Leu His Cys Ser His Pro Leu Gly Ser Leu Ala Leu Gly Gln
                245                 250                 255

Ser Pro Gly Val Ser Met Met Ser Ser Val Ser Gly Cys Pro Pro Ser
            260                 265                 270

Pro Ala Tyr Tyr Ser His Ala Thr Tyr His Pro Leu His Pro Asn Leu
            275                 280                 285

Gln Ala His Leu Gly Gln Leu Ser Pro Pro Glu His Pro Gly Phe
    290                 295                 300

Asp Thr Leu Asp Gln Leu Ser Gln Val Glu Leu Leu Gly Asp Met Asp
305                 310                 315                 320

Arg Asn Glu Phe Asp Gln Tyr Leu Asn Thr Pro Gly His Pro Asp Ser
                325                 330                 335

Ala Ala Gly Val Gly Thr Leu Thr Gly His Val Pro Leu Ser Gln Gly
            340                 345                 350

Thr Pro Thr Gly Pro Thr Glu Thr Ser Leu Ile Ser Val Leu Ala Asp
        355                 360                 365

Ala Thr Ala Thr Tyr Tyr Asn Ser Tyr Ser Val Ser
370                 375                 380

<210> SEQ ID NO 41
<211> LENGTH: 388
<212> TYPE: PRT
<213> ORGANISM: Homo Sapiens
<220> FEATURE:
<221> NAME/KEY: MISC_FEATURE
<223> OTHER INFORMATION: Sox7

<400> SEQUENCE: 41

```
Met Ala Ser Leu Leu Gly Ala Tyr Pro Trp Pro Glu Gly Leu Glu Cys
1               5                   10                  15

Pro Ala Leu Asp Ala Glu Leu Ser Asp Gly Gln Ser Pro Pro Ala Val
                20                  25                  30

Pro Arg Pro Gly Asp Lys Gly Ser Glu Ser Arg Ile Arg Arg Pro
            35                  40                  45

Met Asn Ala Phe Met Val Trp Ala Lys Asp Glu Arg Lys Arg Leu Ala
    50                  55                  60

Val Gln Asn Pro Asp Leu His Asn Ala Glu Leu Ser Lys Met Leu Gly
65                  70                  75                  80

Lys Ser Trp Lys Ala Leu Thr Leu Ser Gln Lys Arg Pro Tyr Val Asp
                85                  90                  95

Glu Ala Glu Arg Leu Arg Leu Gln His Met Gln Asp Tyr Pro Asn Tyr
                100                 105                 110

Lys Tyr Arg Pro Arg Arg Lys Lys Gln Ala Lys Arg Leu Cys Lys Arg
            115                 120                 125

Val Asp Pro Gly Phe Leu Leu Ser Ser Leu Ser Arg Asp Gln Asn Ala
130                 135                 140

Leu Pro Glu Lys Arg Ser Gly Ser Arg Gly Ala Leu Gly Glu Lys Glu
145                 150                 155                 160

Asp Arg Gly Glu Tyr Ser Pro Gly Thr Ala Leu Pro Ser Leu Arg Gly
                165                 170                 175

Cys Tyr His Glu Gly Pro Ala Gly Gly Gly Gly Gly Thr Pro Ser
                180                 185                 190

Ser Val Asp Thr Tyr Pro Tyr Gly Leu Pro Thr Pro Pro Glu Met Ser
                195                 200                 205

Pro Leu Asp Val Leu Glu Pro Glu Gln Thr Phe Phe Ser Ser Pro Cys
210                 215                 220

Gln Glu Glu His Gly His Pro Arg Arg Ile Pro His Leu Pro Gly His
225                 230                 235                 240

Pro Tyr Ser Pro Glu Tyr Ala Pro Ser Pro Leu His Cys Ser His Pro
                245                 250                 255

Leu Gly Ser Leu Ala Leu Gly Gln Ser Pro Gly Val Ser Met Met Ser
                260                 265                 270

Pro Val Pro Gly Cys Pro Pro Ser Pro Ala Tyr Tyr Ser Pro Ala Thr
                275                 280                 285

Tyr His Pro Leu His Ser Asn Leu Gln Ala His Leu Gly Gln Leu Ser
                290                 295                 300

Pro Pro Pro Glu His Pro Gly Phe Asp Ala Leu Asp Gln Leu Ser Gln
305                 310                 315                 320

Val Glu Leu Leu Gly Asp Met Asp Arg Asn Glu Phe Asp Gln Tyr Leu
                325                 330                 335

Asn Thr Pro Gly His Pro Asp Ser Ala Thr Gly Ala Met Ala Leu Ser
                340                 345                 350

Gly His Val Pro Val Ser Gln Val Thr Pro Thr Gly Pro Thr Glu Thr
                355                 360                 365

Ser Leu Ile Ser Val Leu Ala Asp Ala Thr Ala Thr Tyr Tyr Asn Ser
                370                 375                 380

Tyr Ser Val Ser
385

<210> SEQ ID NO 42
<211> LENGTH: 419
```

```
<212> TYPE: PRT
<213> ORGANISM: Mus musculus
<220> FEATURE:
<221> NAME/KEY: MISC_FEATURE
<223> OTHER INFORMATION: Sox17

<400> SEQUENCE: 42

Met Ser Ser Pro Asp Ala Gly Tyr Ala Ser Asp Gln Ser Gln Pro
 1               5                  10                  15

Arg Ser Ala Gln Pro Ala Val Met Ala Gly Leu Gly Pro Cys Pro Trp
            20                  25                  30

Ala Glu Ser Leu Ser Pro Leu Gly Asp Val Lys Val Lys Gly Glu Val
            35                  40                  45

Val Ala Ser Ser Gly Ala Pro Ala Gly Thr Ser Gly Arg Ala Lys Ala
 50                  55                  60

Glu Ser Arg Ile Arg Arg Pro Met Asn Ala Phe Met Val Trp Ala Lys
 65                  70                  75                  80

Asp Glu Arg Lys Arg Leu Ala Gln Gln Asn Pro Asp Leu His Asn Ala
                85                  90                  95

Glu Leu Ser Lys Met Leu Gly Lys Ser Trp Lys Ala Leu Thr Leu Ala
            100                 105                 110

Glu Lys Arg Pro Phe Val Glu Ala Glu Arg Leu Arg Val Gln His
            115                 120                 125

Met Gln Asp His Pro Asn Tyr Lys Tyr Arg Pro Arg Arg Arg Lys Gln
130                 135                 140

Val Lys Arg Met Lys Arg Val Glu Gly Gly Phe Leu His Ala Leu Val
145                 150                 155                 160

Glu Pro Gln Ala Gly Ala Leu Gly Pro Glu Gly Arg Val Ala Met
                165                 170                 175

Asp Gly Leu Gly Leu Pro Phe Pro Glu Pro Gly Tyr Pro Ala Gly Pro
            180                 185                 190

Pro Leu Met Ser Pro His Met Gly Pro His Tyr Arg Asp Cys Gln Gly
            195                 200                 205

Leu Gly Ala Pro Ala Leu Asp Gly Tyr Pro Leu Pro Thr Pro Asp Thr
            210                 215                 220

Ser Pro Leu Asp Gly Val Glu Gln Asp Pro Ala Phe Phe Ala Ala Pro
225                 230                 235                 240

Leu Pro Gly Asp Cys Pro Ala Ala Gly Thr Tyr Thr Tyr Ala Pro Val
                245                 250                 255

Ser Asp Tyr Ala Val Ser Val Glu Pro Pro Ala Gly Pro Met Arg Val
                260                 265                 270

Gly Pro Asp Pro Ser Gly Pro Ala Met Pro Gly Ile Leu Ala Pro Pro
            275                 280                 285

Ser Ala Leu His Leu Tyr Tyr Gly Ala Met Gly Ser Pro Ala Ala Ser
            290                 295                 300

Ala Gly Arg Gly Phe His Ala Gln Pro Gln Pro Leu Gln Pro Gln
305                 310                 315                 320

Ala Pro Pro Pro Pro Gln Gln Gln His Pro Ala His Gly Pro Gly
                325                 330                 335

Gln Pro Ser Pro Pro Glu Ala Leu Pro Cys Arg Asp Gly Thr Glu
            340                 345                 350

Ser Asn Gln Pro Thr Glu Leu Leu Gly Glu Val Asp Arg Thr Glu Phe
            355                 360                 365

Glu Gln Tyr Leu Pro Phe Val Tyr Lys Pro Glu Met Gly Leu Pro Tyr
370                 375                 380
```

-continued

Gln Gly His Asp Cys Gly Val Asn Leu Ser Asp Ser His Gly Ala Ile
385                 390                 395                 400

Ser Ser Val Val Ser Asp Ala Ser Ala Val Tyr Tyr Cys Asn Tyr
            405                 410                 415

Pro Asp Ile

<210> SEQ ID NO 43
<211> LENGTH: 414
<212> TYPE: PRT
<213> ORGANISM: Homo sapiens
<220> FEATURE:
<221> NAME/KEY: MISC_FEATURE
<223> OTHER INFORMATION: Sox17

<400> SEQUENCE: 43

Met Ser Ser Pro Asp Ala Gly Tyr Ala Ser Asp Asp Gln Ser Gln Thr
1               5                   10                  15

Gln Ser Ala Leu Pro Ala Val Met Ala Gly Leu Gly Pro Cys Pro Trp
            20                  25                  30

Ala Glu Ser Leu Ser Pro Ile Gly Asp Met Lys Val Lys Gly Glu Ala
            35                  40                  45

Pro Ala Asn Ser Gly Ala Pro Ala Gly Ala Ala Gly Arg Ala Lys Gly
50                  55                  60

Glu Ser Arg Ile Arg Arg Pro Met Asn Ala Phe Met Val Trp Ala Lys
65                  70                  75                  80

Asp Glu Arg Lys Arg Leu Ala Gln Gln Asn Pro Asp Leu His Asn Ala
                85                  90                  95

Glu Leu Ser Lys Met Leu Gly Lys Ser Trp Lys Ala Leu Thr Leu Ala
            100                 105                 110

Glu Lys Arg Pro Phe Val Glu Ala Glu Arg Leu Arg Val Gln His
            115                 120                 125

Met Gln Asp His Pro Asn Tyr Lys Tyr Arg Pro Arg Arg Arg Lys Gln
130                 135                 140

Val Lys Arg Leu Lys Arg Val Glu Gly Gly Phe Leu His Gly Leu Ala
145                 150                 155                 160

Glu Pro Gln Ala Ala Ala Leu Gly Pro Glu Gly Gly Arg Val Ala Met
                165                 170                 175

Asp Gly Leu Gly Leu Gln Phe Pro Glu Gln Gly Phe Pro Ala Gly Pro
            180                 185                 190

Pro Leu Leu Pro Pro His Met Gly Gly His Tyr Arg Asp Cys Gln Ser
            195                 200                 205

Leu Gly Ala Pro Pro Leu Asp Gly Tyr Pro Leu Pro Thr Pro Asp Thr
            210                 215                 220

Ser Pro Leu Asp Gly Val Asp Pro Asp Pro Ala Phe Phe Ala Ala Pro
225                 230                 235                 240

Met Pro Gly Asp Cys Pro Ala Ala Gly Thr Tyr Ser Tyr Ala Gln Val
                245                 250                 255

Ser Asp Tyr Ala Gly Pro Pro Glu Pro Pro Ala Gly Pro Met His Pro
            260                 265                 270

Arg Leu Gly Pro Glu Pro Ala Gly Pro Ser Ile Pro Gly Leu Leu Ala
            275                 280                 285

Pro Pro Ser Ala Leu His Val Tyr Tyr Gly Ala Met Gly Ser Pro Gly
            290                 295                 300

Ala Gly Gly Gly Arg Gly Phe Gln Met Gln Pro Gln His Gln His Gln
305                 310                 315                 320

-continued

```
           His Gln His Gln His His Pro Pro Gly Pro Gly Gln Pro Ser Pro Pro
                           325                 330                 335

Pro Glu Ala Leu Pro Cys Arg Asp Gly Thr Asp Ser Gln Pro Ala
                       340                 345                 350

Glu Leu Leu Gly Glu Val Asp Arg Thr Glu Phe Glu Gln Tyr Leu His
                       355                 360                 365

Phe Val Cys Lys Pro Glu Met Gly Leu Pro Tyr Gln Gly His Asp Ser
                       370                 375                 380

Gly Val Asn Leu Pro Asp Ser His Gly Ala Ile Ser Ser Val Val Ser
           385                 390                 395                 400

Asp Ala Ser Ser Ala Val Tyr Tyr Cys Asn Tyr Pro Asp Val
                       405                 410

<210> SEQ ID NO 44
<211> LENGTH: 30
<212> TYPE: DNA
<213> ORGANISM: artificial
<220> FEATURE:
<223> OTHER INFORMATION: synthetic sequence
<220> FEATURE:
<221> NAME/KEY: misc_feature
<223> OTHER INFORMATION: amplified region from Sox17EK clone

<400> SEQUENCE: 44
ttcgtggaag aggccaagcg gctgcgcgtg                                       30

<210> SEQ ID NO 45
<211> LENGTH: 10
<212> TYPE: PRT
<213> ORGANISM: artificial
<220> FEATURE:
<223> OTHER INFORMATION: synthetic peptide sequence
<220> FEATURE:
<221> NAME/KEY: MISC_FEATURE
<223> OTHER INFORMATION: corresponding amino acid sequence for amplified
      region of Sox17EK clone

<400> SEQUENCE: 45

Phe Val Glu Glu Ala Lys Arg Leu Arg Val
1               5                   10

<210> SEQ ID NO 46
<211> LENGTH: 15
<212> TYPE: DNA
<213> ORGANISM: artificial
<220> FEATURE:
<223> OTHER INFORMATION: synthetic sequence
<220> FEATURE:
<221> NAME/KEY: misc_feature
<223> OTHER INFORMATION: n is A, T, G or C
<220> FEATURE:
<221> NAME/KEY: misc_feature
<223> OTHER INFORMATION: canonical soxf/octf binding motif
<220> FEATURE:
<221> NAME/KEY: misc_feature
<222> LOCATION: (7)..(7)
<223> OTHER INFORMATION: n is a, c, g, or t

<400> SEQUENCE: 46
cattgtnatg caaat                                                       15

<210> SEQ ID NO 47
<211> LENGTH: 14
<212> TYPE: DNA
<213> ORGANISM: artificial
<220> FEATURE:
```

-continued

```
<223> OTHER INFORMATION: synthetic sequence
<220> FEATURE:
<221> NAME/KEY: misc_feature
<223> OTHER INFORMATION: compressed soxf/octf binding motif

<400> SEQUENCE: 47
ctttgtatga aaat                                                           14

<210> SEQ ID NO 48
<211> LENGTH: 81
<212> TYPE: PRT
<213> ORGANISM: Mus musculus
<220> FEATURE:
<221> NAME/KEY: MISC_FEATURE
<223> OTHER INFORMATION: aligned region from murine Sox1 protein

<400> SEQUENCE: 48
```

Asp Arg Val Lys Arg Pro Met Asn Ala Phe Met Val Trp Ser Arg Gly
1               5                   10                  15

Gln Arg Arg Lys Met Ala Gln Glu Asn Pro Lys Met His Asn Ser Glu
            20                  25                  30

Ile Ser Lys Arg Leu Gly Ala Glu Trp Lys Val Met Ser Glu Ala Glu
        35                  40                  45

Lys Arg Pro Phe Ile Asp Glu Ala Lys Arg Leu Arg Ala Leu His Met
    50                  55                  60

Lys Glu His Pro Asp Tyr Lys Tyr Arg Pro Arg Arg Lys Thr Lys Thr
65                  70                  75                  80

Leu

```
<210> SEQ ID NO 49
<211> LENGTH: 81
<212> TYPE: PRT
<213> ORGANISM: Mus musculus
<220> FEATURE:
<221> NAME/KEY: MISC_FEATURE
<223> OTHER INFORMATION: aligned region from murine Sox2 protein

<400> SEQUENCE: 49
```

Asp Arg Val Lys Arg Pro Met Asn Ala Phe Met Val Trp Ser Arg Gly
1               5                   10                  15

Gln Arg Arg Lys Met Ala Gln Glu Asn Pro Lys Met His Asn Ser Glu
            20                  25                  30

Ile Ser Lys Arg Leu Gly Ala Glu Trp Lys Leu Leu Ser Glu Thr Glu
        35                  40                  45

Lys Arg Pro Phe Ile Asp Glu Ala Lys Arg Leu Arg Ala Leu His Met
    50                  55                  60

Lys Glu His Pro Asp Tyr Lys Tyr Arg Pro Arg Arg Lys Thr Lys Thr
65                  70                  75                  80

Leu

```
<210> SEQ ID NO 50
<211> LENGTH: 81
<212> TYPE: PRT
<213> ORGANISM: Mus musculus
<220> FEATURE:
<221> NAME/KEY: MISC_FEATURE
<223> OTHER INFORMATION: aligned region from murine Sox3 protein

<400> SEQUENCE: 50
```

Asp Arg Val Lys Arg Pro Met Asn Ala Phe Met Val Trp Ser Arg Gly
1               5                   10                  15

```
Gln Arg Arg Lys Met Ala Leu Glu Asn Pro Lys Met His Asn Ser Glu
            20                  25                  30

Ile Ser Lys Arg Leu Gly Ala Asp Trp Lys Leu Leu Thr Asp Ala Glu
        35                  40                  45

Lys Arg Pro Phe Ile Asp Glu Ala Lys Arg Leu Arg Ala Val His Met
    50                  55                  60

Lys Glu Tyr Pro Asp Tyr Lys Tyr Arg Pro Arg Arg Lys Thr Lys Thr
65                  70                  75                  80

Leu

<210> SEQ ID NO 51
<211> LENGTH: 81
<212> TYPE: PRT
<213> ORGANISM: Mus musculus
<220> FEATURE:
<221> NAME/KEY: MISC_FEATURE
<223> OTHER INFORMATION: aligned region from murine Sox7 protein

<400> SEQUENCE: 51

Ser Arg Ile Arg Arg Pro Met Asn Ala Phe Met Val Trp Ala Lys Asp
1               5                   10                  15

Glu Arg Lys Arg Leu Ala Val Gln Asn Pro Asp Leu His Asn Ala Glu
            20                  25                  30

Leu Ser Lys Met Leu Gly Lys Ser Trp Lys Ala Leu Thr Leu Ser Gln
        35                  40                  45

Lys Arg Pro Tyr Val Asp Glu Ala Glu Arg Leu Arg Leu Gln His Met
    50                  55                  60

Gln Asp Tyr Pro Asn Tyr Lys Tyr Arg Pro Arg Arg Lys Lys Gln Gly
65                  70                  75                  80

Lys

<210> SEQ ID NO 52
<211> LENGTH: 81
<212> TYPE: PRT
<213> ORGANISM: Mus musculus
<220> FEATURE:
<221> NAME/KEY: MISC_FEATURE
<223> OTHER INFORMATION: aligned region from murine Sox17 protein

<400> SEQUENCE: 52

Ser Arg Ile Arg Arg Pro Met Asn Ala Phe Met Val Trp Ala Lys Asp
1               5                   10                  15

Glu Arg Lys Arg Leu Ala Gln Gln Asn Pro Asp Leu His Asn Ala Glu
            20                  25                  30

Leu Ser Lys Met Leu Gly Lys Ser Trp Lys Ala Leu Thr Leu Ala Glu
        35                  40                  45

Lys Arg Pro Phe Val Glu Glu Ala Glu Arg Leu Arg Val Gln His Met
    50                  55                  60

Gln Asp His Pro Asn Tyr Lys Tyr Arg Pro Arg Arg Arg Lys Gln Val
65                  70                  75                  80

Lys

<210> SEQ ID NO 53
<211> LENGTH: 80
<212> TYPE: PRT
<213> ORGANISM: Mus musculus
<220> FEATURE:
<221> NAME/KEY: MISC_FEATURE
<223> OTHER INFORMATION: aligned region from murine Sox18 protein
```

```
<400> SEQUENCE: 53

Leu Arg Ile Arg Arg Pro Met Asn Ala Phe Met Val Trp Ala Lys Asp
1               5                   10                  15

Glu Arg Lys Arg Leu Ala Gln Gln Asn Pro Asp Leu His Asn Ala Val
            20                  25                  30

Leu Ser Lys Met Leu Gly Lys Ala Trp Lys Glu Leu Asn Thr Ala Glu
        35                  40                  45

Lys Arg Pro Phe Val Glu Glu Ala Glu Arg Leu Arg Val Gln His Leu
    50                  55                  60

Arg Asp His Pro Asn Tyr Lys Tyr Arg Pro Arg Arg Lys Lys Gln Ala
65                  70                  75                  80
```

MUTANT SOX PROTEINS AND METHODS OF INDUCING PLURIPOTENCY

CROSS-REFERENCE TO RELATED APPLICATION

This application is a U.S. National Stage application under §371 of International Application No. PCT/SG2010/000423, filed Nov. 4, 2010, which claims benefit of, and priority from, U.S. provisional patent application No. 61/272,793, filed on Nov. 4, 2009, the contents of each of which are hereby incorporated herein by reference.

FIELD OF THE INVENTION

The present invention relates to mutant Sox proteins and methods and uses thereof for inducing pluripotency in a cell.

BACKGROUND OF THE INVENTION

Regulation of gene expression plays a critical role in cellular differentiation and morphogenesis. Gene regulation requires multiple regulatory events, which involve the assembly of combinations of transcription factors (TFs) on cis-regulatory modules (CRMs). Pluripotent cells have a different gene expression profile than partially or fully differentiated cells and thus different regulatory events likely occur within pluripotent cells. Elucidation of the regulatory events that determine pluripotency as compared to partial or full differentiation of a cell may allow for production of pluripotent cells from differentiated cells. Thus, the deciphering of the "regulatory code" involved in directing pluripotency and differential gene expression profiles within a cell is the subject of intense research.

It is unclear whether a precise arrangement of TF binding sites (TFBSs) is necessary to execute a pluripotency regulatory event (Segal, E. and Widom, J. *Trends Genet.* (2009) 25(8): 335-43). In support for the hypothesis that TFBS placement is constrained, a composite motif has been identified that recruits a Sox2/Oct4 heterodimer to pluripotency CRMs as the core regulatory unit (Chen, X. et al., *Cell* (2008) 133: 1106-1117; Boyer, L. A. et al., *Cell* (2005) 122: 947-952; Loh, Y. H. et al., *Nat. Genetics* (2006) 38:431-40). It is possible that differently configured composite motifs recruit different Sox/Oct pairs that build the core of regulatory complexes in various cell types and for varying levels and types of cellular differentiation.

The Sox and POU (Oct) families of transcription factors consist of 20 and 14 members respectively, and often act synergistically during vertebrate development (reviewed in Bowles, J. et al., *Dev. Biol.* (2000) 227: 239-55; Ryan, A. K. & Rosenfield, M. G. *Genes & Dev.* (1997) 11: 1207-25; Wegner, M. *Nucleic Acid Res* (1999) 27: 1409-20). Despite their diverse biological roles the specificity of Sox proteins for DNA elements is largely indistinguishable and the amino acids involved in specific DNA contacts are highly conserved (Badis, G. et al. *Science* (2009) 324(5935):1720-3). Therefore, any single transcription factor may not be specific; rather, specificity in transcriptional control may instead be achieved as a result of selective heterodimerization. Indeed, several distinct Sox/POU pairs have been implicated as key regulators of cellular fates: Sox2/Oct4 are essential factors in (ES) cells (Boyer, L. A. et al., *Cell* (2005) 122: 947-952; Loh, Y. H. et al., *Nat. Genetics* (2006) 38:431-40; Rodda, D. J. et al. *J Biol Chem* (2005) 280:24731-7); Sox2/Brn2 was found important in neural development (Tanaka, S. et al. *Mol Cell Biol* (2004) 24: 8834-46); Sox11/Brn1 pair regulates glial cells (Kuhlbrodt, K. et al. *J Biol Chem* (1998) 273: 16050-7); and Sox17 has been shown to cooperate with Oct4 during mesendoderm formation (Stefanovic, S. et al. *J Cell Biol* (2009) 186: 665-73).

SUMMARY OF THE INVENTION

Exhaustive efforts have been extended in the search for reprogramming factors that turn differentiated cells into induced pluripotent stem (iPS) cells. Yet, only a few proteins are capable of this feat and their biochemical uniqueness remains unexplained. For example, Sox2 can induce iPS cells, but Sox17, despite binding to similar DNA sequences, cannot.

The present invention involves mutated Sox proteins that have acquired or increased ability to induce pluripotency in a partially differentiated or fully differentiated cell. Sox7 and Sox17 are mutated to resemble in part Sox2, or Sox2 is mutated to resemble in part Sox7 or Sox17.

To understand these mechanistic differences, variant sox/oct DNA motifs were identified, including a novel compressed sox/oct motif in mouse embryonic stem cells. It was discovered that Sox2 and Sox17 exhibit inverse preferences to assemble with Oct4 on the canonical versus the compressed motif. The present invention relates to the discovery that the preferences of Sox2 and Sox17 can be swapped by mutating amino acid residues within the protein contact interface that binds to Oct4. These results were also extended to Sox7. This mutagenesis prevents the formation of an Oct4/Sox17 complex on the compressed motif and enhances cooperative interaction on the canonical motif. Strikingly, the re-engineered Sox 7 and Sox17 are able to promote reprogramming and convert cells to induced pluripotent cells, likely by introducing dimers formed with Oct4 on pluripotency enhancer elements. In certain embodiments, even mutation of a single acidic residue in Sox7 or Sox17 results in a change in preference for the various DNA motifs, and provides these recombinant proteins with the ability to induce pluripotency in a cell that is partially or fully differentiated.

Thus, Sox 7 and Sox17 are able to induce pluripotency once mutated to bind to the appropriate DNA motifs. It was observed that the mutated Sox7 and Sox17 may exhibit greater efficiency of inducing pluripotency than that observed with wildtype Sox2. Accordingly, it was found that mutants of Sox2 that were created using the high mobility group domain of Sox2 together with the C-terminal activation domain of Sox7 or Sox17 resulted in an increased pluripotency induction efficiency of Sox2. Thus, the present invention also relates to the discovery that replacing the C-terminal activation domain of Sox2 with that of Sox7 or Sox17 increases the pluripotency induction efficiency of Sox2.

The mutated Sox proteins of the present invention may be used to induce pluripotency in a cell that has partially or fully differentiated and thus has lost pluriopotency. Thus, the present invention also relates to methods and uses of the mutant Sox proteins for inducing pluripotency in a cell.

Thus, in one aspect, the present invention provides a mutant Sox7 or Sox17 protein comprising a mutation in any of amino acids 88 to 108 of a Sox7 or amino acids 111 to 131 of a Sox17 protein wherein the mutant Sox7 or Sox17 protein is capable of conversion of a non-pluripotent cell to a pluripotent cell.

In another aspect, the present invention provides a mutant Sox7 or Sox17 protein comprising a mutation in the amino acid sequence encoding the Oct4 protein contact interface of a Sox7 or Sox17 protein wherein the mutant Sox protein can induce conversion of a non-pluripotent cell to a pluripotent cell.

The mutant Sox protein is a mutant Sox7 protein in one embodiment, and is a mutant Sox17 protein in another embodiment.

In the mutant Sox7 or Sox17 protein, any amino acid residue in the sequence LSQKRPYVDEAERLRLQHMQD [SEQ ID NO: 36] or LAEKRPFVEEAERLRVQHMQD [SEQ ID NO: 37] may be substituted with a different amino acid. In some embodiments, the glutamic acid located at amino acid 99 of the Sox7 or amino acid 122 of the Sox17 protein is mutated. In some embodiments, the glutamic acid located at amino acid 99 of the Sox7 or amino acid 122 of the Sox17 protein is substituted with lysine.

The mutant Sox7 or Sox17 protein may be a human Sox7 or Sox17 protein.

In another aspect, the present invention provides a nucleic acid molecule encoding a mutant Sox protein as described herein.

In another aspect, the present invention provides a mutant Sox protein comprising an amino acid sequence encoding a high mobility group domain of a Sox2 protein and a C-terminal activation domain of a Sox7 protein or a Sox17 protein.

The C-terminal activation domain may be the C-terminal activation domain of a Sox7 protein or may be the C-terminal activation domain of a Sox17 protein.

In another aspect, the present invention provides a cell expressing a mutant Sox protein as described herein.

In another aspect, the present invention provides a cell comprising a nucleic acid encoding a mutant Sox protein as described herein.

In another aspect, the present invention provides a method of inducing conversion of a non-pluripotent cell to a pluripotent cell, the method comprising culturing the non-pluripotent cell in the presence of i) a mutant Sox protein as described herein; ii) Oct4; and iii) at least one of c-myc and Klf4 and in conditions suitable for growth of embryonic stem cells.

In another aspect, the present invention provides a method of inducing conversion of a non-pluripotent cell to a pluripotent cell, the method comprising co-expressing in the non-pluripotent cell i) a mutant Sox protein as described herein; ii) Oct4; and iii) at least one of c-myc and Klf4 from one or more expression vectors and culturing the non-pluripotent cell in conditions suitable for growth of embryonic stem cells.

The non-pluripotent cell may be a fibroblast or a mesenchymal stem cell. In one embodiment, the non-pluripotent cell is an embryonic fibroblast. In one embodiment, the non-pluripotent cell is an adipose-tissue derived mesenchymal stem cell.

The non-pluripotent cell may be a human cell.

The non-pluripotent cell may be a partially differentiated cell or may be a fully differentiated cell.

Other aspects and features of the present invention will become apparent to those of ordinary skill in the art upon review of the following description of specific embodiments of the invention in conjunction with the accompanying figures.

BRIEF DESCRIPTION OF THE DRAWINGS

The figures, which illustrate, by way of example only, embodiments of the present invention, are as follows.

DETAILED DESCRIPTION

Figure 1:
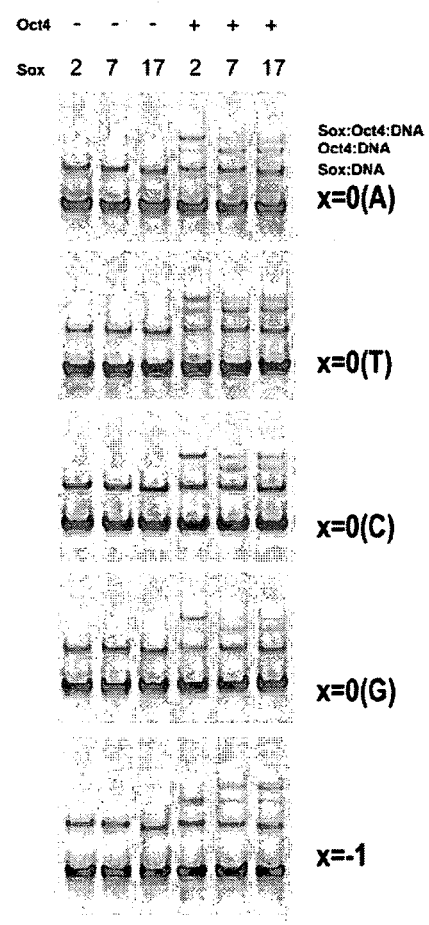
FIG. 1: EMSAs to assess Sox7, Sox2HMGs and spacer nucleotides.

Here, recombinant engineered Sox2, Sox7 and Sox17 proteins are described that may be used induce a cell that is not pluripotent to become pluripotent.

The recombinant engineered proteins possess features from Sox2 and from Sox7 or Sox17. A Sox2, Sox7 or Sox17 is used as the base sequence and the sequence is then adapted to include a feature from Sox7 or Sox17 (if the starting sequence is Sox2) or to include a feature from Sox2 (if the starting sequence is Sox7 or Sox17).

Each of Sox2, Sox7 and Sox17 refers to a highly conserved family of proteins. Reference to a Sox2, Sox7 or Sox17 protein that is used as the starting sequence prior to effecting the mutations as described herein, includes reference to any Sox2, Sox7 or Sox17 protein that retains the ability to interact with Oct4 and to direct the specific function of that Sox2, Sox7 and Sox17, for example either the induction or maintenance of pluripotency for Sox2, or the developmental role in endodermal differentiation of Sox7 or Sox17. The Sox2, Sox7 or Sox17 starting sequence may be a native or wildtype Sox2, Sox7 or Sox17, or may be any fragment, homologue or mutant that retains the native activity of the Sox2, Sox7 or Sox17, as the case maybe. The starting sequence of Sox2, Sox7 or Sox17 prior to any mutations as described herein may have one, two, three, four, five, ten or more amino acid insertions, substitutions (including conservative amino acid substitutions) or deletions, provided that the native activity of the Sox protein is maintained.

The Sox2, Sox7 or Sox17 protein used as a starting sequence may be any Sox2, Sox7 or Sox17 protein, for example from any eukaryotic organism that develops from a pluripotent stem cell, for example an insect, plant or mammalian Sox2, Sox7 or Sox17 protein, including a mouse protein or a human protein. The Sox2, Sox7 or Sox17 may be the same species as the cell in which pluripotency is to be induced, or it may be from a different species given the high degree of homology in each of the Sox2, Sox7 and Sox17 protein families, provided that the relevant Sox protein is able to function as the native endogenous protein within that species of cell.

In some embodiments, the Sox2 sequence, used as the starting sequence prior to effecting the mutations as described herein, comprises, consists essentially of, or consists of one of the following sequences, or is a protein having 80% or greater, 85% or greater, 90% or greater, 95% or greater sequence identity with one of the following sequences:

From mouse:
[SEQ ID NO.: 38]
MYNMMETELKPPGPQQASGGGGGGGNATAAATGGNQKNSPDRVKRPMNAF

MVWSRGQRRKMAQENPKMHNSEISKRLGAEWKLLSETEKRPFIDEAKRLR

ALHMKEHPDYKYRPRRKTKTLMKKDKYTLPGGLLAPGGNSMASGVGVGAG

LGAGVNQRMDSYAHMNGWSNGSYSMMQEQLGYPQHPGLNAHGAAQMQPMH

RYDVSALQYNSMTSSQTYMNGSPTYSMSYSQQGTPGMALGSMGSVVKSEA

SSSPPVVTSSSHSRAPCQAGDLRDMISMYLPGAEVPEPAAPSRLHMAQHY

QSGPVPGTAINGTLPLSHM

From human:
[SEQ ID NO.: 39]
MYNMMETELKPPGPQQTSGGGGNSTAAAAGGNQKNSPDRVKRPMNAFMV

WSRGQRRKMAQENPKMHNSEISKRLGAEWKLLSETEKRPFIDEAKRLRAL

HMKEHPDYKYRPRRKTKTLMKKDKYTLPGGLLAPGGNSMASGVGVGAGLG

AGVNQRMDSYAHMNGWSNGSYSMMQDQLGYPQHPGLNAHGAAQMQPMHRY

DVSALQYNSMTSSQTYMNGSPTYSMSYSQQGTPGMALGSMGSVVKSEASS

SPPVVTSSSHSRAPCQAGDLRDMISMYLPGAEVPEPAAPSRLHMSQHYQS

GPVPGTAINGTLPLSHM

In some embodiments, the Sox7 sequence, used as the starting sequence prior to effecting the mutations as described herein, comprises, consists essentially of, or consists of one of the following sequences, or is a protein having 80% or greater, 85% or greater, 90% or greater, 95% or greater sequence identity with one of the following sequences:

From mouse:
[SEQ ID NO.: 40]
MASLLGAYPWTEGLECPALEAELSDGLSPPAVPRPSGDKSSESRIRRPMN

AFMVWAKDERKRLAVQNPDLHNAELSKMLGKSWKALTLSQKRPYVDEAER

LRLQHMQDYPNYKYRPRRKKQGKRLCKRVDPGFLLSSLSRDQNTLPEKNG

IGRGEKEDRGEYSPGATLPGLHSCYREGAAAAPGSVDTYPYGLPTPPEMS

PLDALEPEQTFFSSSCQEEHGHPHHLPHLPGPPYSPEFTPSPLHCSHPLG

SLALGQSPGVSMMSSVSGCPPSPAYYSHATYHPLHPNLQAHLGQLSPPPE

HPGFDTLDQLSQVELLGDMDRNEFDQYLNTPGHPDSAAGVGTLTGHVPLS

QGTPTGPTETSLISVLADATATYYNSYSVS

From human:
[SEQ ID NO.: 41]
MASLLGAYPWPEGLECPALDAELSDGQSPPAVPRPPGDKGSESRIRRPMN

AFMVWAKDERKRLAVQNPDLHNAELSKMLGKSWKALTLSQKRPYVDEAER

LRLQHMQDYPNYKYRPRRKKQAKRLCKRVDPGFLLSSLSRDQNALPEKRS

GSRGALGEKEDRGEYSPGTALPSLRGCYHEGPAGGGGGGTPSSVDTYPYG

LPTPPEMSPLDVLEPEQTFFSSPCQEEHGHPRRIPHLPGHPYSPEYAPSP

LHCSHPLGSLALGQSPGVSMMSPVPGCPPSPAYYSPATYHPLHSNLQAHL

GQLSPPPEHPGFDALDQLSQVELLGDMDRNEFDQYLNTPGHPDSATGAMA

LSGHVPVSQVTPTGPTETSLISVLADATATYYNSYSVS

In some embodiments, the Sox17 sequence, used as the starting sequence prior to effecting the mutations as described herein, comprises, consists essentially of, or consists of one of the following sequences, or is a protein having 80% or greater, 85% or greater, 90% or greater, 95% or greater sequence identity with one of the following sequences:

From mouse:
[SEQ ID NO.: 42]
MSSPDAGYASDDQSQPRSAQPAVMAGLGPCPWAESLSPLGDVKVKGEVVA

SSGAPAGTSGRAKAESRIRRPMNAFMVWAKDERKRLAQQNPDLHNAELSK

MLGKSWKALTLAEKRPFVEEAERLRVQHMQDHPNYKYRPRRRKQVKRMKR

VEGGFLHALVEPQAGALGPEGGRVAMDGLGLPFPEPGYPAGPPLMSPHMG

PHYRDCQGLGAPALDGYPLPTPDTSPLDGVEQDPAFFAAPLPGDCPAAGT

YTYAPVSDYAVSVEPPAGPMRVGPDPSGPAMPGILAPPSALHLYYGAMGS

PAASAGRGFHAQPQQPLQPQAPPPPPQQQHPAHGPGQPSPPPEALPCRDG

TESNQPTELLGEVDRTEFEQYLPFVYKPEMGLPYQGHDCGVNLSDSHGAI

SSVVSDASSAVYYCNYPDI

From human:
[SEQ ID NO.: 43]
MSSPDAGYASDDQSQTQSALPAVMAGLGPCPWAESLSPIGDMKVKGEAPA

NSGAPAGAAGRAKGESRIRRPMNAFMVWAKDERKRLAQQNPDLHNAELSK

MLGKSWKALTLAEKRPFVEEAERLRVQHMQDHPNYKYRPRRRKQVKRLKR

VEGGFLHGLAEPQAAALGPEGGRVAMDGLGLQFPEQGFPAGPPLLPPHMG

-continued

GHYRDCQSLGAPPLDGYPLPTPDTSPLDGVDPDPAFFAAPMPGDCPAAGT

YSYAQVSDYAGPPEPPAGPMHPRLGPEPAGPSIPGLLAPPSALHVYYGAM

GSPGAGGGRGFQMQPQHQHQHQHHPPGPGQPSPPPEALPCRDGTDPSQ

PAELLGEVDRTEFEQYLHFVCKPEMGLPYQGHDSGVNLPDSHGAISSVVS

DASSAVYYCNYPDV

As used herein, "consists essentially of" or "consisting essentially of" means that the relevant Sox protein (Sox2, Sox7 or Sox17) used as a starting sequence prior to any mutations as described herein, includes one or more amino acids, including at one or both ends peptide, but that the additional amino acids do not materially affect the function of the Sox protein. For example, the Sox protein may have one, two, three, four or five, ten, fifteen or twenty amino acids at one or both ends of the described sequences as described herein, provided that such a Sox protein still possesses the native function of the relevant Sox protein, such as inducing or maintaining pluripotency for Sox2 or differentiation of the endoderm for Sox7 and Sox17.

The putative Oct4 interaction surface of Sox17 displays a markedly different electrostatic interface when compared to that of Sox2, potentially affecting the ability of Sox17 to interact with Oct4 (Palasingam, P. et al. *J Mol Biol* (2009) 388: 619-30). Despite binding to DNA with essentially the same characteristics as Sox2, Sox7 and Sox17 bring about fundamentally different developmental effects. Sox2 is required for the development of the epiblast (Avilion, A. A. et al. *Genes Dev* (2003) 17:126-40), neural lineages (Zappone, M. V. et al. Development (2000) 127: 2367-82), and many other developmental processes (Que, J. *Development* (2009) 136:1899-1907; Que, J. *Development* (2007) 134:2521-31; Okubo, T. *Genes Dev* (2006) 20:2654-59), while Sox17 is found in the extraembryonic and definitive endoderm lineages of the embryo (Kanai-Azuma, M. et al. Development (2002) 129:2367-79). Sox17, when forcibly expressed in mouse and human ES cells pushes the cells towards an endodermal-like cell fate (Seguin C. A., et al. *Cell Stem Cell* (2008) 3: 182-95; Shimoda, M. et al. *J. Cell Sci.* (2007) 120:3859-69), and crucially Sox17 cannot replace Sox2 in converting fibroblast cells into induced-pluripotent stem cells (iPS) (Nakagawa, M. et al. *Nat Biotechnol* (2008) 26:01-6). This demonstrates that despite binding similar DNA-sequence motifs Sox2 and Sox17 have highly divergent developmental capabilities. Sox7, like Sox17, is involved in endoderm differentiation of mouse and human ES cells (Seguin C. A., et al. *Cell Stem Cell* (2008) 3: 182-95).

Thus, in one aspect there is provided a mutant protein that comprises a Sox2 protein or a Sox7 or Sox17 protein that has one or more amino acids replaced with one or more corresponding amino acids from a Sox7 or Sox17 protein or from a Sox2 protein, which mutant protein is capable of inducing conversion of a non-pluripotent cell to a pluripotent cell. Reference to replacing an amino acid with a corresponding amino acid from another protein is reference to replacing a given amino acid with a given Sox2, Sox7 or Sox17 protein with the amino acid or amino acids or a domain defined by a sequence of amino acids from another Sox7, Sox17 or Sox2 protein, which replacing amino acids are in the corresponding position based on sequence alignment and sequence identity and homology, or which possess the corresponding function, for example the activation domain.

The mutant Sox2, Sox7 or Sox17 protein is capable of inducing, or induces, pluripotency, meaning that when the Sox2, Sox7 or Sox17 mutant is expressed in (or is added into) a non-pluripotent cell that has the additional protein factors involved in inducing and maintaining pluripotency such as Oct4, Klf4 and c-Myc, the non-pluripotent cell is converted to a pluripotent cell under suitable growth conditions. Such pluripotency conversion can be confirmed using standard techniques to identify known pluripotency markers, for example, Eras, Nanog, Oct4, Sox2, Zfp206 or Zic3. The Examples below describe techniques that may be used to confirm conversion of a non-pluripotent cell to a pluripotent cell.

The mutant protein is an engineered, recombinant protein. The mutant protein may be an isolated protein or may be introduced into a cell using molecular cloning and recombinant technologies, including transfection, transduction or transformation of the cell with a nucleic acid molecule encoding the mutant protein for expression in the cell. The mutant Sox2, Sox7 or Sox17 protein may be any Sox2, Sox7 or Sox17 protein, for example insect, plant, mammalian Sox2, Sox7 or Sox17 protein, including a mouse protein or a human protein.

The mutant protein may be a mutant Sox7 or Sox17 protein that has been altered in one or more of the residues forming the Oct4 protein contact interface. The alteration includes insertion, deletion or substitution to change the one or more altered residues, or to change a region within the mutant protein, to the amino acid residue or region of Sox2 that corresponds to or is analogous to the residues in Sox7 or Sox17 that are being altered. That is, after alteration, the specific sequence in the Sox7 or Sox17 Oct4 protein contact interface that has been altered then has the sequence of the specific corresponding or analogous residues from the Sox2 Oct4 protein contact interface.

For example, the engineered mutant Sox7 may be a human or mouse Sox7 altered at one or more residues in the sequence LSQKRPYVDEAERLRLQHMQD [SEQ ID NO.: 36] or a human or mouse Sox7 altered at one or more residues in residues 88 to 108. The mutant Sox7 may have E99 changed to a basic residue, for example K or R. In one embodiment, the mutant Sox7 has the mutation E99K.

For example, the engineered mutant Sox17 may be a human or mouse Sox17 altered at one or more residues in the sequence LAEKRPFVEEAERLRVQHMQD [SEQ ID NO.: 37] or a human or mouse Sox17 altered at one or more residues in residues 111 to 131. The mutant Sox7 may have E122 changed to a basic residue, for example K or R. In one embodiment, the mutant Sox7 has the mutation E122K.

In one particular embodiment, the mutant protein is Sox7E99K. In another particular embodiment, the mutant protein is Sox17E122K.

Alternatively, the mutant protein may be a mutant Sox2 protein that has been altered in one or more of the residues forming the C-terminal activation domain. The alteration includes insertion, deletion or substitution to change the one or more altered residues, or to change a sequence within the mutant protein, to the sequence of Sox7 or Sox17 that corresponds to or is analogous to the residues in Sox2 that are being altered. That is, after alteration, the specific sequence in the Sox2 C-terminal activation domain that has been altered then has the sequence of the specific corresponding or analogous residues from the Sox7 or Sox17 C-terminal activation domain.

In some embodiments, the entire C-terminal activation domain of Sox2 is replaced with the entire activation domain of Sox7 or Sox17. For example, amino acids 122 to 320 of mouse Sox2 may be replaced with amino acid residues 147 to 420 of mouse Sox17 or the corresponding residues from mouse Sox7. Similar alterations based on the human sequences may also be made.

Sequences of Sox2, Sox7 and Sox17 are known, including wildtype or unmutated sequences, including mouse and human Sox2, Sox7 and Sox17 proteins. As well, the regions within Sox2 and Sox7 and Sox17 that function as the Oct4 protein contact interface and the C-terminal activation domain are known. Thus, the sequences of the mutant proteins as described herein may be readily designed using standard knowledge in the art.

The mutant Sox2, Sox7 or Sox17 protein may be produced using standard molecular engineering and cloning techniques. For example, techniques for producing a mutant protein having a mutation at one or more amino acid residues are known, including primer extension, PCR and cloning techniques that involve primers containing suitable nucleic acid residue changes to encode the mutant protein.

Thus, also contemplated is a nucleic acid molecule that encodes a mutant protein as described herein. As indicated above, the protein sequences of the mutant proteins may be readily identified using knowledge and skill in the art. Similarly, using the genetic code and knowledge of the degeneracy of the code, nucleic acid molecules that encode a mutant protein as described herein may be readily designed and synthesized using standard molecular cloning techniques. As will be appreciated, the nucleic acid molecule may further comprise additional elements, for example a promoter region operably linked to the sequence encoding the mutant protein, for example the promoter being a promoter that is expressed in embryonic stem cells.

Also contemplated is a cell expressing the mutant Sox protein as described herein, or a nucleic acid molecule encoding such a mutant Sox protein, including a cell in vitro.

The mutant proteins and the nucleic acid molecules encoding such mutant protein as described herein may be used to induce pluripotency by converting a non-pluripotent cell to a pluripotent cell, including in in vitro methods.

Methods of inducing pluripotency are known, for example as described in Takahashi and Yamanaka (2006) *Cell* 126: 663-676. Briefly, pluripotency protein factors Sox2, Oct4, and one or both of c-Myc and Klf4 are contacted with or co-expressed within the cell that is to be induced to be pluripotent and the cell is grown under conditions that are suitable for and that promote growth of embryonic stem cells.

In the present methods, Sox2 is replaced by a mutant protein as described herein. The cell in which pluripotency is to be induced may already express one or more of the pluripotency factors aside from Sox2, such as Oct4 and one or both of c-Myc and Klf4. Alternatively, the cell may be altered, for example by transfection or transformation, to express Oct4 and one or both of c-Myc and Klf4. In the methods as described below, the partially or fully differentiated cell requires addition of Oct4 and one or both of c-Myc and Klf4, although it will be appreciated that one or more of these factors may already be expressed by the cell.

Thus, there is provided a method of inducing conversion of a non-pluripotent cell to a pluripotent cell, the method comprising culturing the non-pluripotent cell in the presence of a mutant protein as described herein together with Oct4, and at least one of c-Myc and Klf4, under conditions suitable for growth of embryonic stem cells. The method may be performed as an in vitro method.

The cell may be any non-pluripotent cell, for example any cell that is partially differentiated or fully differentiated, including an in vitro cell, a cell in culture, an explanted cell from a subject. The non-pluripotent cell may be from any multi-cellular eukaryotic organism that develops from pluripotent cells, including an insect cell, a plant cell or a mammalian cell, including for example a mouse cell or a human cell. The cell may be any type of partially or fully differentiated cell, including for example an embryonic fibroblast cell, such as a human or mouse embryonic fibroblast, or for example a mesenchymal stem cell, such as a human or mouse adipose-tissue derived mesenchymal stem cell.

As used herein, the term cell refers to and includes a single cell, a plurality of cells or a population of cells where context permits, unless otherwise specified. Similarly, reference to cells also includes reference to a single cell where context permits, unless otherwise specified.

Culturing the cell in the context of the mutant Sox2, Sox7 or Sox17 together with Oct4 and one or both of c-Myc and Klf4 includes contacting the cell with the various pluripotency protein factors so that the pluripotency protein factors are taken up by the cell, as well as transfecting or transducing the cell with nucleic acids encoding the various pluripotency protein factors and co-expressing the pluripotency protein factors. As used herein, reference to pluripotency protein factors is reference to the mutated Sox protein as described herein, Oct4, and one or both c-Myc and Klf4.

As will be appreciated, co-expression of the pluripotency protein factors will involve expression from a suitable promoter that is operably linked to the coding region for the particular pluripotency protein factor. A first nucleic acid sequence is operably linked with a second nucleic acid sequence when the sequences are placed in a functional relationship. For example, a coding sequence is operably linked to a promoter if the promoter activates the transcription of the coding sequence.

Once the cell has been contacted with the pluripotency protein factors, or once the cell has been transfected or transduced with nucleic acid molecules encoding each of the pluripotency protein factors and the cell has been exposed to conditions for co-expression, the cells may be cultured under conditions suitable for growth of embryonic stem cells. Embryonic stem cell media are known and are commercially available. In some circumstances, it may be desirable to use feeder cells to promote stem cell growth in culture, in keeping with standard embryonic stem cell culture techniques.

If preferred, individual colonies of induced pluripotent cells may be selected and then expanded in order to obtain a clonal population of an induced pluripotent cell, in accordance with standard cell culture techniques.

The present methods and uses are further exemplified by way of the following non-limiting examples.

EXAMPLES

Example 1

The role of the Sox2/Oct4 pair as an inducer of pluripotency is well established (Nichols, *Cell* (1998) 95:379-91; Rodda, D. J. et al. *J Biol Chem* (2005) 280:24731-7) and there is evidence that Sox17 and Oct4 functionally cooperate during endodermal differentiation (Reim, G., et al. *Dev Cell* (2004) 6:91-101; Stefanovic, S. et al. *J Cell Biol* (2009) 186: 665-73).

It is therefore conceivable that Sox2 and Sox17 can compete for Oct4 and form stable complexes on specific genomic regions characterized by distinct cis-regulatory motifs.

To test this, experiments were designed to identify variant sox/oct motif configurations in genomic regions occupied by Sox2 and Oct4 in mouse ES cells (Chen, X. et al., *Cell* (2008) 133: 1106-1117), the results of which experiments identified a novel compressed element. In vitro heterodimerization assays, however, revealed that only Sox17/Oct4 but not Sox2/Oct4 was able to co-bind this element while the Sox2/Oct4 complex predominates on the canonical site. By designing mutations using structural models, point mutations were generated that swapped the heterodimerization preferences of Sox2 and Sox17. Strikingly, this change in the capability of Sox17/Oct4 dimerization now converted Sox17 into a potent reprogramming factor.

Experimental Procedures

Computational Analysis: To search for different sox/oct motif configurations the motif derived from the Oct4/Sox2 ChIP-seq data (Chen, X. et al., Cell (2008) 133: 1106-1117) was used and a position-weight matrix (pwm) search tool was applied to scan through sets of FASTA sequences for the presence of this motif.

To construct different configurations of the sox/oct motif, variants of the motifs were generated by inserting unbiased base pairs within or between the sox/oct motif, or by making reverse complement versions of the respective motifs. This allowed for construction of many different hypothetical configurations of the sox/oct motif, from the canonical (soxf_0bp_octf), order (octf_0bp_soxf), convergent (soxf_0bp_octr; f and r signify the strand of the motif element) and divergent (octr_0bp_soxf). Pwms with a spacer base pair inserted in between (soxf_0bp_octf, soxf_1bp_octf . . . soxf_10bp_octf) were also constructed, as were 'compressed' pwms, by eliminating a base pair between the sox and oct parts of the motif (labelled: soxf_-1bp_octf, octf_-1bp_soxf, etc).

Log-odds base position weight matrix finding and the implementation: The motif discovery tool was implemented as a simple position weight matrix scoring tool, essentially as described in Ben-Gal, I. et al., Bioinformatics (2005) 21:2657-2666 as a Markov(0) model. The algorithm includes some background correction. This type of algorithm is commonly referred to as a log-odds model and more sophisticated models of transcription factor binding and discovery are available (reviewed in van Loo, P. and Marynen, P. Briefings in Bioinformatics (2009) 10:509-524). The advantage of the log-odds model is its ease of implementation and rapid scanning speed on modern computer hardware.

Position frequency matrices (pfm) were converted into position weight matrices (pwm) using the following formula:

$$w_{p,n} = \log 2[(f_{p,n} + \sqrt{(N_p)} \cdot b_n)/(N_p + \sqrt{(N_p)})/b_n]$$

where w is the weight of a particular nucleotide at each position p in the matrix for each nucleotide n. f is the number of occurrences of each nucleotide n at position p, N is the total number of occurrences of A, C, G and T nucleotides at this position p. b is the expected background for this nucleotide n, which was assumed to be equal, i.e. [0.25, 0.25, 0.25, 0.25]. This is a reasonable assumption for promoter regions (here, considered as ~10kb of transcription start sites) which in human and mouse are roughly 25% each of A, C, T, G, but this assumption does not hold distal to promoter regions which tend to become CG rich. No further corrections were made for background variations.

To scan a section of DNA sequence, the following formula was used to determine a score at each possible position for the motif:

$$s = (\Sigma[w_{p,n}] - m)/(M - m)$$

where s=the normalised score between 0 and 1, w is the weight for the actual nucleotide n at position p, M is the maximum possible score for the pwm and m is the minimum possible score for the pwm (calculated by summing all of the minimum or maximum values for the pwm at each column in the pwm matrix).

A simple log-odds motif discovery tool (nicknamed: PMF) was implemented in Python (versions>2.5<3.0).

Threshold estimation, and Chip-seq sequence window size: Searching with a pwm relies on the setting of an arbitrary threshold above which a particular motif is accepted and below which the motif is discarded. It was known that the motif was enriched in the Sox/Oct ChIP-seq list from (Chen, X. et al., Cell (2008) 133: 1106-1117) so that ChIP-seq list was used and, as a negative control, a singleton-GFP list was used, a list of single mapped reads derived from an anti-GFP ChIP-seq result (Chen, X. et al., Cell (2008) 133: 1106-1117). The singleton-GFP list is believed to be representative of the proportion of the genome available for sequencing, and hence already includes potential sequencing bias, yet is otherwise randomly distributed across the 'sequence-able genome'.

Figure 3:
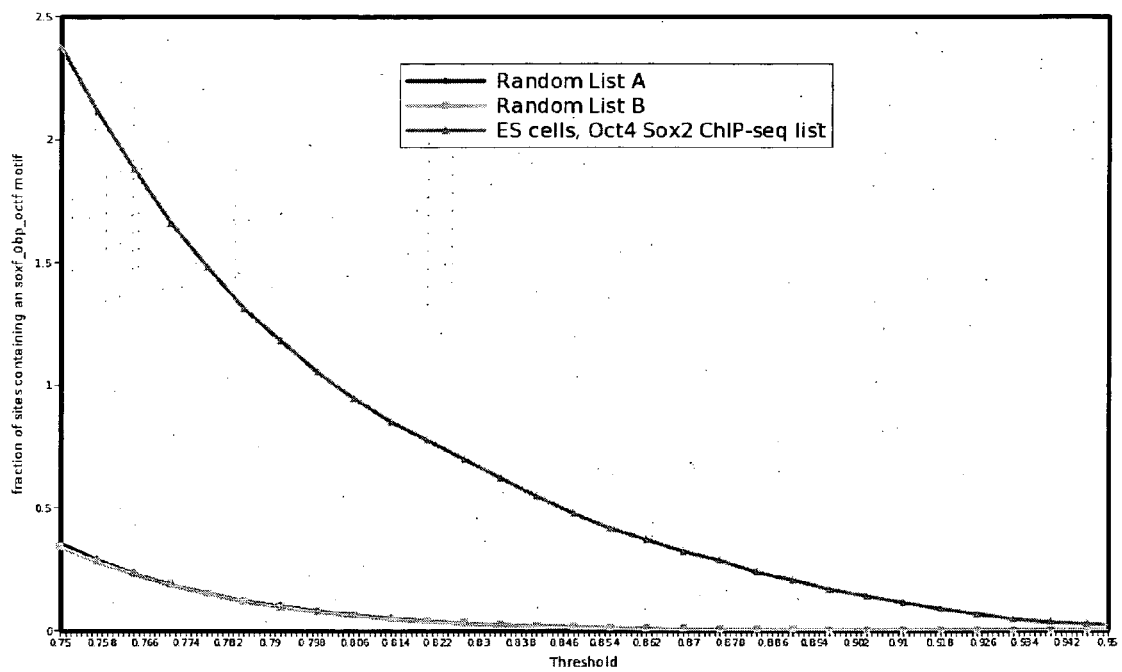
FIG. 3: Identification of a threshold for the canonical Soxf_0bp_octf motif.

The canonical sox/oct motif (soxf_0bp_octf) was scanned against a list of FASTA sequences derived from the Sox/Oct ChIP-seq or a randomly sampled list of 10,000 singleton-GFP sites. The centre point of the coordinates was taken and the window was expanded by 100 bp in each direction. To establish the optimal motif discovery threshold, the threshold was varied from 0.8 to 1.0 and the Sox2/Oct4 and the singleton-GFP lists were then scanned. At a motif threshold of 0.82, 5% of the motifs in the singleton-GFP list were found as compared to in the same number of Sox2/Oct4 bound sequences (FIG. 3).

Figure 4A:
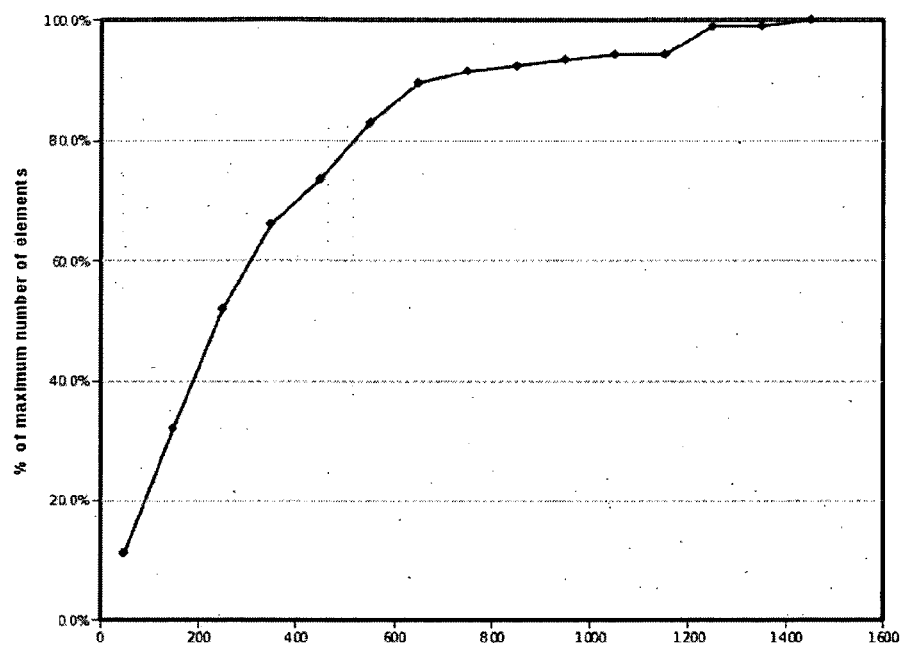
FIG. 4: Expanded search window used in search for true motifs.
Figure 4B:
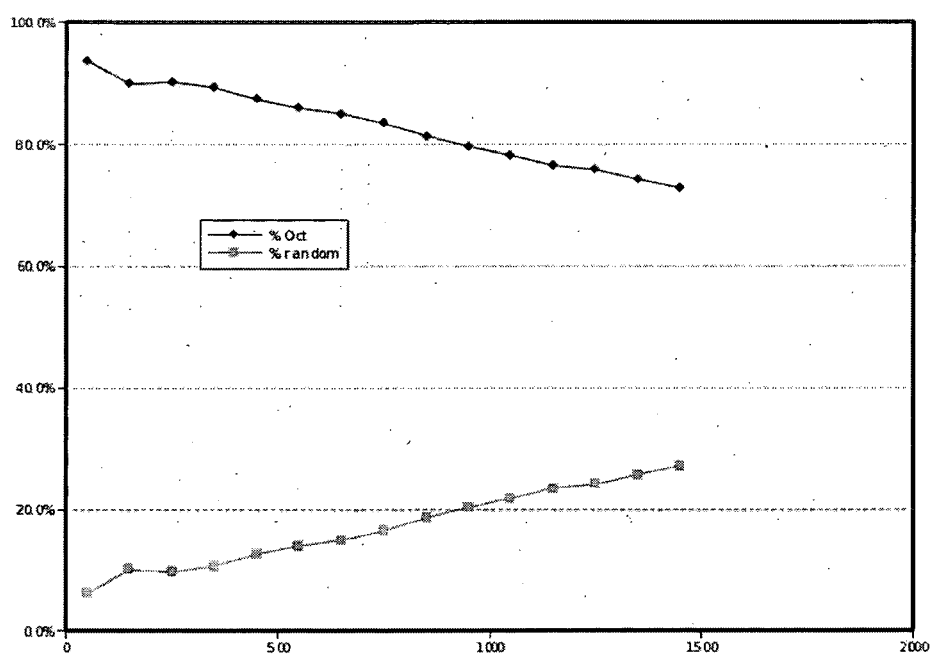

Next, the influence of the size of the FASTA window has on the discovery of motifs was investigated. The peaks from the Sox2/Oct4 ChIP-seq do not have a resolution that exactly pinpoints the bonafide binding site, a majority of likely sites seem to fall very close (within the range of ~25 bp) of the centre of the ChIP-seq site (FIG. 4). To assess the effect of the size of the sequence window on the number of recovered motifs, a very large window of 750 bp's either side of the centre of the ChIP-seq peak was used. The size of the motif was then reduced and the motifs were scored as a percentage of all the motifs within ±750bps of the centre of the ChIP-seq (FIG. 4). We settled on a window size of ±100 bps, as it includes over 50% of all the possible sox/oct motifs within ±1kb, but minimises the number of motifs discovered by chance alone.

Collection and modification of motifs: The motif used in this study was taken from Chen, X. et al., Cell (2008) 133: 1106-1117 and was de novo derived from the Oct4 Chip-seq experiment. The matrix is as follows (represented in Python code):

```
soxf_0bp_octf = matrix('soxf_0bp_octf',

[[4, 43, 0, 8], #c-sox2 start

[37, 0, 0, 25], #a/t

[0, 0, 0, 79], #t

[4, 11, 0, 64], #t

[14, 2, 54, 8], #g

[9, 3, 17, 62], #t-sox2 end

[13, 58, 4, 24], #c/g#

[99, 0, 0, 0], #a-oct4 start

[0, 0, 0, 99], #t
```

-continued

[4, 0, 84, 12], #*g*

[42, 42, 4, 4], #*a/c*

[40, 39, 0, 4], #*a/c*

[56, 3, 12, 2], #*a*

[62, 0, 0, 1], #*a*

[16, 0, 2, 29]]) #*a/t*-end *oct4*

To insert unbiased base pairs into the matrix, a single unbiased nucleotide was inserted into the matrix: [1,1,1,1]. Converting this pfm to a pwm will result in the following pwm matrix for that base pair: [0,0,0,0]. As this does not affect the minimum or maximum scores for the particular pwm, this approach should have only a minimal bias on the ability of a matrix to find a particular sequence in the genome. The soxf_10 bp_octf matrix is represented in Python like this:

soxf_10bp_octf = matrix('soxf_10bp_octf',

[[4, 43, 0, 8], #*c-sox2* start

[37, 0, 0, 25], #*a/t*

[0, 0, 0, 79], #*t*

[4, 11, 0, 64], #*t*

[14, 2, 54, 8], #*g*

[9, 3, 17, 62], #*t-sox2* end

[13, 58, 4, 24], #*c/g*

[1, 1, 1, 1],

[1, 1, 1, 1],

[1, 1, 1, 1],

[1, 1, 1, 1],

[1, 1, 1, 1],

[1, 1, 1, 1],

[1, 1, 1, 1],

[1, 1, 1, 1],

[1, 1, 1, 1],

[1, 1, 1, 1],

[1, 1, 1, 1],

[99, 0, 0, 0], #*a-oct4* start

[0, 0, 0, 99], #*t*

[4, 0, 84, 12], #*g*

[42, 42, 4, 4], #*a/c*

[40, 39, 0, 4], #*a/c*

[56, 3, 12, 2], #*a*

[62, 0, 0, 1], #*a*

[16, 0, 2, 29]]) #*a/t*-end *oct4*

Figure 5:
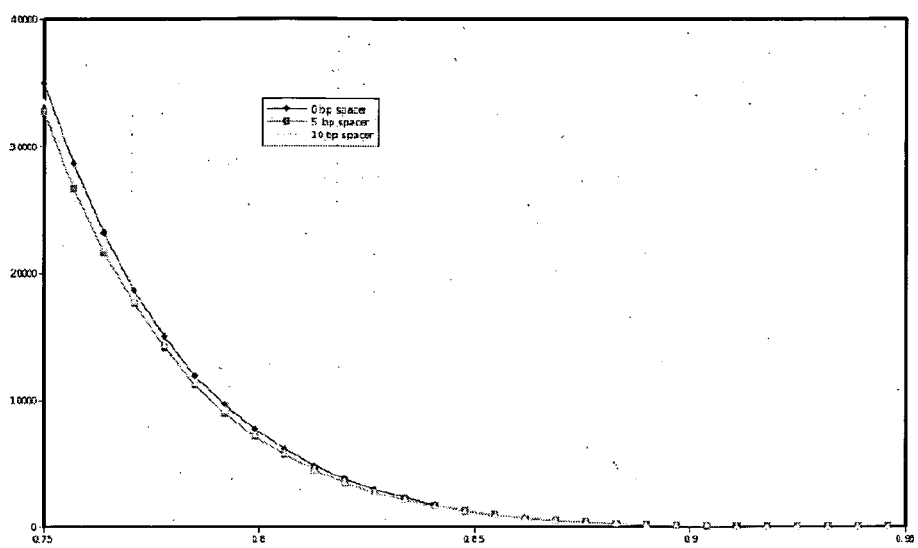
FIG. 5: Insertion of unbiased bases into the motif does not significantly affect the motifs ability to discover sequences.

Next, it was test whether insertion of these unbiased base pairs would affect the frequency of matches against a random list (FIG. 5), on the reasoning that a random list (here generated from a random selection of 'singletons' from the anti-GFP immunoprecipitation) would be useful as no significant enrichment of the canonical soxf_0bp_octf motif would be expected. FIG. 5 shows that insertion of the unbiased base pairs does not significantly affect the number of motifs discovered in the same random list using either a canonical motif (soxf_0bp_octf) compared to a 5 bp or 10 bp spacer (soxf_5bp_octf, soxf_10bp_octf, respectively). The full results of the pwm scan against the Sox/Oct list is presented in FIG. 6.

Demonstration the PIVMs for the Canonical and Compressed Motifs Retrieve Different Sequences: All the 15-mer and 14-mer sequences were retrieved that the canonical and compressed pwm matches at the chosen threshold of 0.82. Common sequences between the two pwm's and palindromic elements are contained in the data were identified. The canonical motif matches 106,630 15-mers from 1,073,741,824 possible 15-mers while the compressed pwm matched 39,138 14-mer sequences from a possible 268,435,456. When the two sets of sequences were overlapped, 9216 sequences were found to be in common—ie. 9216 15-mer sequences can be detected by both the canonical and compressed motifs. However, the number of 15-mer sequences that matched either the compressed or canonical motif is considerably larger (97,414 and 29,922 sequences respectively). This underlines that although there is overlap between the compressed and canonical motif where they can both identify the same DNA sequence, in actuality they are distinct entities.

Recombinant Sox proteins: The HMG domains of mouse Sox2, Sox? and Sox17 were cloned and heterologously expressed and purified to homogeneity as described elsewhere (Palasingam, P. et al. *J Mol Biol* (2009) 388: 619-30). An extended version of the Sox2HMG (denoted Sox2HMG1 spanning amino acids 33-141 of the full length protein, swissprot-id P48432) was cloned using the TOPO technology followed by a transfer into the pETG20A expression plasmid using the GATEWAY LR technology and purified using established procedures (Ng et al., 2008).

Production of recombinant Oct4 protein: The POU domain of mouse Oct4 (residues 126-289 of the full length protein, swissprot id P20263) was produced as follows. Oct4-POU was introduced into the pENTR/TEV/D-TOPO vector by directional TOPO cloning and transferred into the pETG40A expression plasmid. The fusion protein containing an N-terminal MBP tag was expressed in BL21(DE3) cells by growing in Luria Bertani (LB) medium supplemented with 0.2% Glucose and 100 µg/ml Ampicillin at 37° C. to $OD_{600}$ of ~0.6-0.8 before adding 0.5mM iso-propyl-beta-thio galactoside (IPTG) for induction at 25° C. for 5 hours. Cell pellet was resuspended in buffer A (20 mM HEPES pH 7.0; 200 mM NaCl; mM EDTA; 10 mM β-merceptoethanol) and disrupted by sonification at 35ampitude with 2s-on/4s-off for 15 min at 4° C. The MBP-fusion proteins were first purified using Amylose beads then cleaved using tobacco etch virus (TEV) protease at 4° C. overnight to remove the MBP tag. Cleaved protein was further purified using a Resource-S (GE Healthcare) column and eluted with a linear NaCl gradient over 10 column volumes. Fractions containing only cleaved Oct4-POU protein were pooled, exchanged into a storing buffer (10 mM HEPES pH7.0; 100 mM NaCl) using PD-10 (GE Heathcare) and concentrated using VIVASPIN 3MWCO columns (Sartorius).

Site-directed Mutagenesis: Amino acid substitutions were introduced using the QuikChange-XL site-directed mutagenesis kit (Stratagene) and GATEWAY entry clones with DNA oligos listed in Table 1. Sequencing was performed to verify the successful change of amino acids. Recombinant mutant proteins were expressed and purified as described for the wildtype constructs above.

TABLE 1

DNA Oligomers

| OLIGO NAME (CLONING TECHNOLOGY) | SEQUENCE | SEQ ID NO. |
|---|---|---|
| I. Oligos used to generate GATEWAY entry clones | | |
| mouse Sox2HMGlong (TOPO) | Forward: CACCATGGGCGGCAACCAGAAGA<br>Reverse: TTACATGCTGTTCCCGCCGGGGGCCAGCAA | 1<br>2 |
| mouse Oct4POU (TOPO) | Forward: CACCCCCGAGGAGTCCCAGG<br>Reverse: TCATTCTCGTTGGGAATACTCAATA | 3<br>4 |
| mouse Sox2 full (BP) | Forward: GGGGACAAGTTTGTACAAAAAAGCAGGCTTCacc ATGTATAACATGATGGAGACGGAG<br>Reverse: ggggaccactttgtacaagaaagctgggtTCACATGTGCGACAGGGGCAG | 5<br>6 |
| mouse Sox17 full (BP) | Forward: GGGGACAAGT TTGTACAAAA AAGCAGGCTTCaccatgagcagcccggatgc<br>Reverse: ggggaccactttgtacaa-gaaagctgggtTTAAATGTCGGGGTAGTTGC | 7<br>8 |
| II. Oligos used to mutagenize Sox proteins (only forward oligo shown) | | |
| Sox2$^{KE}$ | CATCGACGAGGCCGAGCGGCTGCGCGCTCTG | 9 |
| Sox2$^{\alpha 17}$ | GAGAAGCGGCCGTTCGTCGAGGAGGCCGAGCGGCT GCGCGTTCAGCACATGCAGGACCACCCGAATTATAAATACCGG | 10 |
| Sox17$^{EK}$ | GTGGAAGAGGCCAAGCGGCTGCGCGTGCAG | 11 |
| III. Oligos used to validate retroviral inserts from iPS cells | | |
| pMX-forward | GGGTGGACCATCCTCTAGACT | 12 |
| Sox17-reverse | TCAAATGTCGGGGTAGTTGC | 13 |
| Sox2-reverse | GGGCAGTGTGCCGTTAAT | 14 |
| Klf4-reverse | AAGGCCCTGTCACACTTCTG | 15 |
| Pou5f1-reverse | CAGTTTGAATGCATGGGAGA | 16 |
| c-myc-reverse | TGTTCTCGTCGTTTCCTCAA | 17 |
| IV. Oligos used for EMSA (only forward oligo shown) | | |
| -1 | CGGCGCGGCATTGTATGCAAATCGGCGGCG | 18 |
| 0 | GGCGCGGCATTGTCATGCAAATCGGCGGCG | 19 |
| 1 | GGCGCGGCATTGTCGATGCAAATCGGCGGC | 20 |
| 2 | GCGCGGCATTGTCGGATGCAAATCGGCGGC | 21 |
| 3 | GCGCGGCATTGTCGGCATGCAAATCGGCGG | 22 |
| 4 | CGCGGCATTGTCGGGCATGCAAATCGGCGG | 23 |
| 5 | CGCGGCATTGTCGGGCGATGCAAATCGGCG | 24 |
| 6 | GCGGCATTGTCCGGGCGATGCAAATCGGCG | 25 |
| 7 | GCGGCATTGTCCGGGCGGATGCAAATCGGC | 26 |
| 8 | CGGCATTGTCGCGGGCGGATGCAAATCGGC | 27 |
| 9 | CGGCATTGTCGCGGGCGGCATGCAAATCGG | 28 |
| 10 | GGCATTGTCCGCGGGCGGCATGCAAATCGG | 29 |
| Order | GGCGCGGATGCAAATCATTGTCCGGCGGCG | 30 |
| Convergent | GGCGCGGCATTGTCATTTGCATCGGCGGCG | 31 |
| Divergent | GGCGCGGGACAATGATGCAAATCGGCGGCG | 32 |

TABLE 1-continued

DNA Oligomers

| OLIGO NAME (CLONING TECHNOLOGY) | SEQUENCE | SEQ ID NO. |
|---|---|---|
| Sox tandem | GCGGCATTGTCCATTGTCATGCAAATCGGC | 33 |
| Nanog | CATGGACATTGTAATGCAAAAGAAGCTG | 34 |
| Nanog' (-1) | CTGGACATTGTATGCAAAAGAA | 35 |

Electrophoretic mobility shift assays: All EMSAs were carried out using double-stranded 5' Cy5-labeled DNA (Sigma Proligo, see Table 1) (Jauch, R., et al. J. Mol. Biol. (2008) 376(3):758-70). Binding buffer contains 20 mM Tris-HCl pH 8.0, 50 µM $ZnCl_2$, 100 mM KCl, 10% glycerol, 2 mM 13-merceptoethanol, 0.1 mg/ml bovine serum albumin (BSA) and 0.1% (v/v) Igepal CA-630. 250nM dsDNA probes were mixed with analyte proteins singly or in combinations in binding buffer and incubated for 1 hr at 4° C. in dark. Samples were loaded into a pre-run 12% (w/v) IX Tris-glycine polyacrylamide gel in 1XTG (25 mM Tris, pH 8.3; 192 mM glycine) buffer to separate different species of bound and unbound probes. The fluorescence was detected using a Typhoon 9140 PhosphorImager (Amersham Biosciences).

Generation of iPS: The iPS assay was carried out using procedures modified from Takahashi and Yamanaka (2006) Cell 126:663-676. Mouse embryo fibroblasts (MEF) were reprogrammed to iPS cells by retroviral transduction of transcription factors following established protocols (Takahashi and Yamanaka (2006) Cell 126:663-676). MEF were isolated from C57B16 mice in which green fluorescence protein (GFP) is driven by Oct4 promoter (Jackson Laboratory). For retroviral production, pMX plasmids expressing Oct4, Klf4, c-Myc, Sox2, Sox17, Sox17EK, Sox2KE, or Sox2a17 were individually transfected, with Fugene transfection reagent (Roche), into PLAT-E viral packaging cells (Cell Biolabs) together and virus-containing media that was collected after 2 days. Infections with freshly prepared retrovirus plus 4 µg/ml polybrene were carried out on 6 cm plates seeded with 267,000 Oct4-GFP MEF and 800,000 inactivated feeder fibroblasts. Retrovirus-containing media for Oct4, Klf4, and c-Myc were mixed, in equal volumes, with Sox2, Sox17, Sox17EK, Sox2KE or Sox2α17. Fresh medium containing DMEM High Glucose, 10% FBS and 1% L-glutamine (Gibco) was provided after two days. Cell culture conditions were switched to ES cell medium on third day. Oct4-GFP+ iPS colonies were counted three weeks later and representative clones isolated. Selected colonies were transferred into 96-well plates containing PBS, followed by trypsinization for 5 minutes, and then single-cell suspensions were transferred into 48-well dishes with inactivated fibroblast feeders. Picked iPS cells were further expanded on feeders in 6 cm and 10 cm dishes under ES cell culture conditions.

Quantitative real-time PCR (Q-RT-PCR): Expression of marker genes by iPS clones was performed by Q-RT-PCR. In order to minimize genomic DNA contamination, RNA was extracted with TriZol reagent (Invitrogen), and further purified with the RNeasy minikit (Qiagen). cDNA was synthesized with 1.0 µg total RNA using the High Capacity cDNA Archive kit (Applied Biosystems). For each Q-PCR reaction, cDNA samples diluted 10× in water were mixed with 10 ul TaqMan® Universal PCR Master Mix reagent (Applied Biosystems), and 1 µl of a single TaqMan probe from the following list: Eras, Zic3, Oct4, Nanog, Sox2, and Zfp206 (20× TaqMan® Gene Expression Assay reagents; Applied Biosystems) in a final volume of 20 µl. Q-RT-PCR analysis was conducted in 96 well clear optical reaction plate (Applied Biosystems) on the ABI Prism 7900 instrument.

Immunostaining: To test for expression of pluripotency markers SSEA-1. and Sox2, immunostaining was conducted on iPS clones cultured without feeder cells in 48-well plates. iPS ells were fixed with 4% paraformaldehyde and permeabilized with 0.5% Triton X-100. Primary antibodies (Millipore) against SSEA-1 (10 ug/ml) and Sox2 (10 ug/ml) were incubated with fixed cells for 2 hours at room temperature, and subsequently stained with secondary antibody conjugated to Alexa Fluor 594 (Molecular probes) (4 ug/ml) for 1 hour at room temperature in the dark. Images were captured using a ZEISS Axioobservor DI inverted fluorescence microscope (Carl Zeiss International).

Figure Legends

FIG. 1: EMSAs to assess Sox7, Sox2HMGs and spacer nucleotides. To exclude artifacts that could have been caused by the length difference between the Sox2/Sox17 constructs, the differential assembly of the core Sox2HMG domain (termed Sox2HMGs) was tested. The domain spans the same range of amino acids of the Sox17 construct. The differential assembly of Sox7, another F group Sox protein with strong sequence similarities to Sox17 was also tested. Sox7 and Sox17 had comparably weak Oct4 heterodimerization on canonical elements whereas cooperative binding was observed on the compressed element. Thirdly, the spacer nucleotide of the canonical element on the remaining three possible nucleotides was varied (CATTGT(C/A/T/G)ATG-CAAAT). The identity of the spacer nucleotide was found not to have a pronounced impact on the overall dimerization profile of the various Sox protein with Oct4. 50nM of Sox2HMGs, Sox7HMG and Sox17HMG were incubated with canonical elements containing different basebairs at position 7 of the Sox motif $(C_1A_2T_3T_4G_5T_6(A/T/C/G)_7$; A-D) and on the compressed element (E) in the absence (Lanes 1-3) or presence (Lanes 4-6) of 250 nM Oct4POU.

Figure 2:
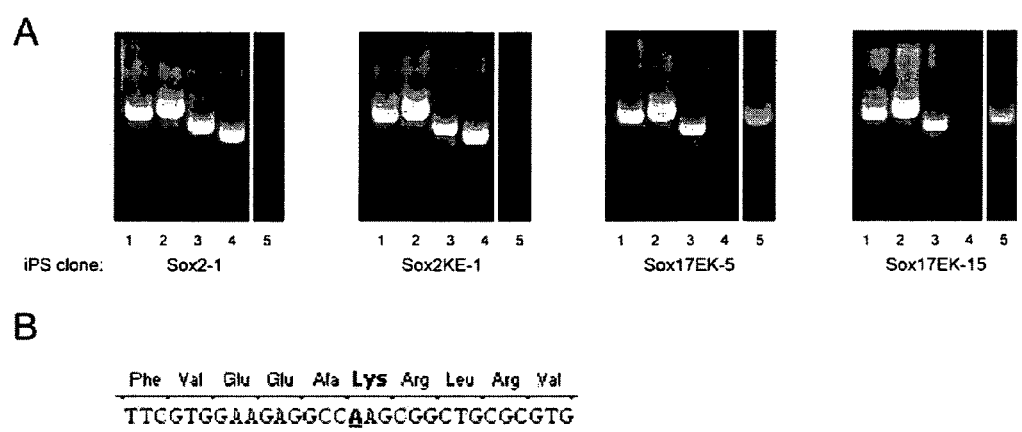
FIG. 2: Confirmation of retroviral transduction in iPS clones derived by Sox2, Sox2KE, or Sox17EK. Panel A shows results of PCR amplification of genomic DNA derived from each of the indicated iPS clones using a vector specific primer and gene specific primers for c-myc, Klf4, Oct4, Sox2, and Sox17, lanes 1-5, respectively. Panel B shows the amplified region of a Sox17EK clone (SEQ ID NOs.: 44 and 45).

FIG. 2: Confirmation of retroviral transduction in iPS clones derived by Sox2, Sox2KE, or Sox17EK. A. PCR amplification of genomic DNA derived from the indicated iPS clones was performed with a vector specific primer and gene specific primers for c-myc, Klf4, Oct4, Sox2, and Sox17 (Table 1), lanes 1-5, respectively.

Specific amplifications of the correct fragment sizes confirmed that there was retroviral integration of the transduced genes. B. The PCR primers for Sox2 and Sox17 did not distinguish the alternative alleles of these two genes, therefore, DNA sequencing of the amplified fragments from Sox17EK clones was performed and confirmed the presence of E to K mutation.

FIG. 3: Justification for a threshold for the canonical Soxf_0bp_octf motif

FIG. 4: Expansion of the search window does not greatly help the discovery of true motifs. The ChIP-seq results were used and the search window was increased from 50 bp through 1400 bp and the number of motifs was then counted, expressed as a percentage of the number of motifs discovered when the window was at its widest. A. As the window expands the probability of finding motifs by chance alone also increases. B. Generated by performing the same count, but in a random list.

FIG. 5: Insertion of unbiased bases into the motif does not significantly affect the motifs ability to discover sequences. At all thresholds the insertion of an unbiased base pair did not significantly alter the number of motifs discovered in the same random list of FASTA sequences (10,000).

Figure 6:
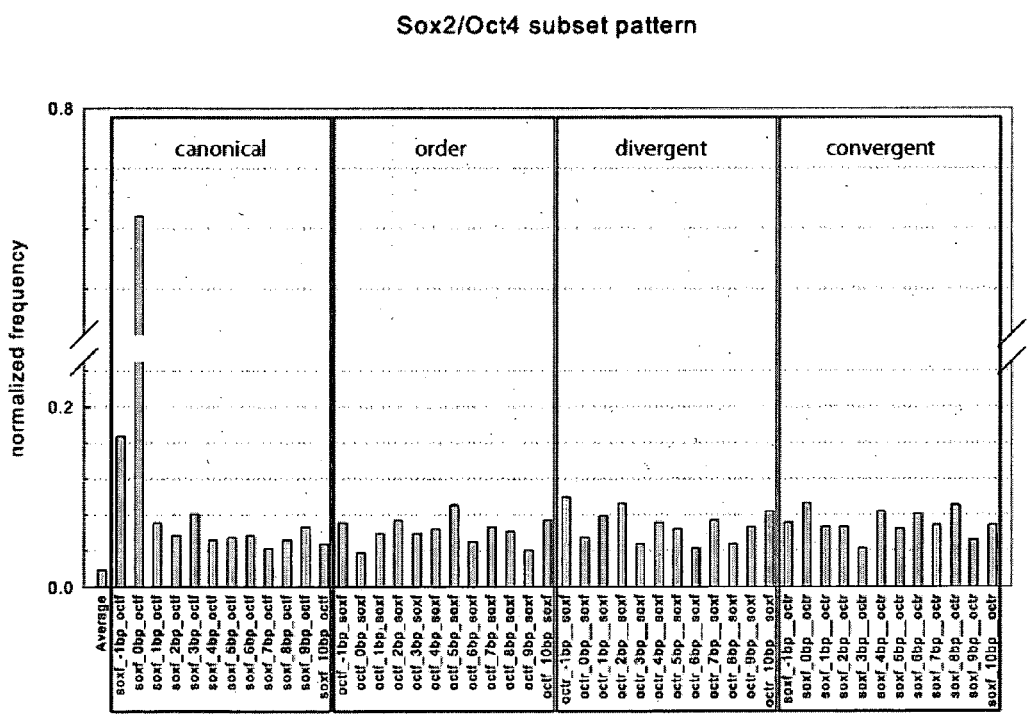
FIG. 6: The full table of variant motifs scanned against the Sox2/ Oct4 ChIP-seq results.

FIG. 6: The full table of variant motifs scanned against the Sox2/Oct4 ChIP-seq results.

FIG. 7: in silico discovery of sox/oct variant motifs. (A) schematic of the variant motifs generated in this study. All the combinations were explored with 0 to 10 bp's of spacer between the sox and oct parts of the motif, also a 'compressed' motif was created by deleting the base pair between the sox and oct motif. (B) Frequency of returned number of hits for the canonical variant motifs with −1, 1 through 10 bp's of spacer. The frequency of motif is expressed here percentage increase over a random list of genomic coordinates. A second independently generated random list is included for comparison. (C) The WebLogo's of the returned motifs discovered by the pwm matching tool. (D) Percentage increase over background of motif against the different ChIP-seq lists derived from Chen, X. et al., Cell (2008) 133: 1106-1117, 'Oct4/Sox2' is an overlap list containing all of the overlapping Oct4/Sox2 bound sites. The 'Oct4' and 'Sox2' lists contain all of the Oct4 and Sox2 binding sites respectively.

FIG. 8: Differential assembly of Sox2HMG and Oct4POU (A) and Sox17HMG and Oct4 (D) on a series of different motif configurations. Motif configurations were systematically designed as outlined in FIG. 1A using 30bp DNA elements containing identical Sox (CATTGTC) and Oct4 (ATGCAAAT) consensus sequences flanked by GC rich sequences. To minimize binding anomalies due to cryptic elements at the periphery or within the spacer region we used idealized motifs (CATTGTC for sox and ATGCAAAT for oct) and introduced G's and C's as spacer and boundary nucleotides. Each DNA element was mixed with individual transcription factor proteins as well as with both Sox2 and Oct4 DBDs in combination (See supplementary information). 250 nM of every cy5-labelled DNA element was incubated with 50 nM Sox2HMG1/Sox17HMG and 250 nM Oct4POU proteins alone and in combination followed by PAGE to assess the formation of ternary Sox/Oct4/DNA complex. The position of the various protein DNA complexes are marked by arrows. The number of spacer basepairs is indicated above and below the gels. X=−1 denotes the compressed and X=0 the canonical elements. The co-occurrence of canonical and compressed motifs within genomic regions co-bound by Sox2 and Oct4 in mouse embryonic stem cells are depicted in (B). The significance of the overlap as compared to a randomly generated list was established using a binomial test. (C) shows the portion of motifs with shared genomic coordinates.

FIG. 9: (A and B) Differential assembly of Sox2/Oct4 and Sox17/Oct4 on the compressed (A) and canonical (B) elements. Proteins were added to 250 nM DNA elements in the sequences indicated above the lanes. To distinguish shifts caused by Sox2 and Sox17 a N and C-terminally extended Sox2-HMG (Sox2 HMG1) domain was used in these experiments. As a consequence, both the Sox2/DNA and the Sox2/Oct4/DNA complex migrate slower than the corresponding Sox17 complexes, allowing us to visualize a Sox2/Oct4 and Sox17/Oct4 DNA complex on the same gel. Protein-DNA mixtures were incubated for 10 minutes before the next protein component was added. Sox2 and Sox17 were kept at 50 nM and Oct4POU at 250 nM final concentration. Sox2/Oct4/ DNA complexes and Sox17/Oct4/DNA complexes are marked by solid boxes. Expected position but absent or low abundance Sox2 or Sox17 ternary complexes are marked by dotted boxes. Binary protein/DNA complexes are marked by arrows. (C) Model summarizing the differential assembly of Sox2/Oct4 and Sox17/Oct4 on the canonical versus the compressed element. Cooperative binding is concluded when the formation of a ternary complex is favored over the formation of binary complexes (i.e. if Oct4 containing DNA complexes are fully supershifted if a Sox protein is present).

FIG. 10: (A) Alignment of the amino acid sequence of all mouse Sox proteins. The Sox subfamilies (Bowles, J. et al., Dev. Biol. (2000) 227: 239-55) are indicated to the right. The numbering corresponds to the Sox17 sequence. Alpha helices are marked with a red bar. The FM wedge is indicated with an orange bar below the alignment and further DNA interacting residues are marked by black closed circles. Highly conserved and similar sequences are shaded in black or gray. The position of glutamate and lysine residues distinguishing Sox17 and Sox2 is marked by an arrow. The eight amino acids in helix 3 of Sox2 that were replaced by their corresponding counterparts found in Sox17 to construct the Sox2$^{\alpha17}$ protein are indicated. (B) Structural model prepared using pymol by using the structural coordinates for Sox17 and the Sox2/Oct1 on DNA. The van-der-Waals surface of the DNA derived from the Sox2/Oct1 structure is shown in light gray. Sox17 (medium gray) was superimposed onto Sox2 (light gray). Oct1 is shown in black. Note that the linker region connecting the POU specific and the POU homedomain is not present in the NMR derived model due to structural disorder. The glutamate (Sox17) and the lysine (Sox2) that were mutated are shown as ball-and-sticks. Note that the lysine exists in two alternative conformations in the NMR model. (C) Point mutations at the Sox/Oct4 interface swap the differential assembly behavior of Sox2 and Sox17 on the canonical versus the compressed element. DNA element derived from a functional sox/oct element within the Nanog enhancer were used (Rodda, D.J. et al. J Biol Chem (2005) 280:24731-7). 2 denotes Sox2 HMGs, 17: Sox17HMG, 2KE: Sox2KE, 17EK: Sox17EK and 2α17 the replacement of all Sox2 residues in helix 3 that differ from the corresponding Sox17 residues into their Sox17 counterpart. Sox proteins were incubated with DNA individually and in combination with Oct4. Positions of binary Sox/DNA and Oct4/DNA as well as of ternary Sox/Oct4/DNA complexes are indicated.

FIG. 11: Characterization of iPS clones reprogrammed by Sox17EK. A. Combined bright field and fluorescent photographs are presented of isolated iPS colonies. Shown are representative clones of iPS cells derived from MEFs that were transduced with Oct4, c-myc, Klf4 plus Sox2 (a and b) or Sox17EK (c and b). The MEF cells contained a GFP reporter driven from the Oct4 promoter, thus, iPS generation was scored by the appearance of GFP-positive colonies Individual Oct4-GFP+iPS colonies were isolated and passaged on a feeder layer of inactivated fibroblast 21 days after retroviral transduction. Scale bars are 100 um. B. Q-RT-PCR was performed to determine expression of pluripotency genes by iPS clones reprogrammed by Sox2, Sox17EK, or Sox2KE, as indicated Gene expression levels of the six indicated pluripotency markers (relative to nontransduced MEFs) from three replicate wells are presented as average ± confidence intervals. For comparison, the expression levels of the pluripotency markers in a mouse ES cell line(E14) and in MEFs are also presented. C Uniform expression of SSEA-1 and Sox2 on iPS clones. Three individual iPS clones (C15, C5, and C6), induced from MEFs by OCK plus Sox17EK, were immunostained for expression of the pluripotency markers SSEA-1 (a, e, and i) and Sox2 (c, g, and k). Oct4-GFP expression for the same fields are also presented (b, d, f, h, j, and l). Scale bars are 100 um (e, f, i, j) and 200 um (a-d, g, h, k, and l).

Results

Figure 7A:
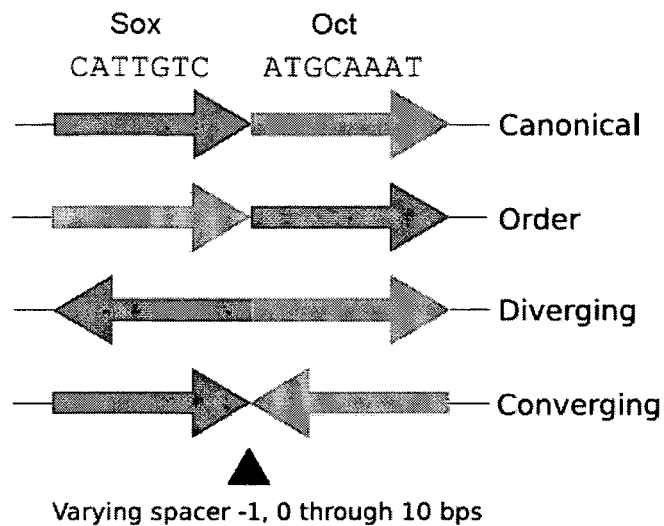
FIG. 7: In silico discovery of sox/oct variant motifs; the predominant sequences in the WebLogo's are included as SEQ ID NOs: 46 (for the canonical motif) and 47 (for the compressed motif).
Figure 7B:
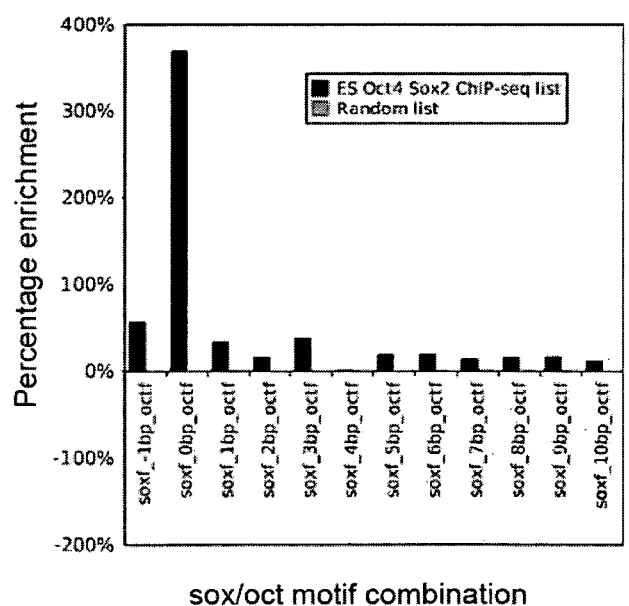

Analysis of sox/oct motif configurations in mouse ESC: A position weight matrix (PWM) scanning tool was devised to quantify the occurrence of different configurations of the Sox2/Oct4 composite motif. The spacing between Sox2 and Oct4 motifs was systematically assessed, including the order and the motif orientations (FIG. 7A). For motif scans, 200 bp windows of the mouse genome were interrogated that have been shown by ChIP to be occupied by Sox2 and Oct4 in embryonic stem cells (Chen, X. et al., Cell (2008) 133: 1106-1117). Motif frequencies for differently spaced sox/oct in the canonical orientation (soxf_nbp_octf where f denotes the forward orientation, r the reverse complement and n the number of spacer base pairs) are detailed in FIG. 7B (see FIG. 6 for a complete list). As expected, the canonical sox/oct motif was most strongly enriched (370% above background). Many of the other motifs with spacer nucleotides inserted were found to be only modestly enriched.

Figure 7C:
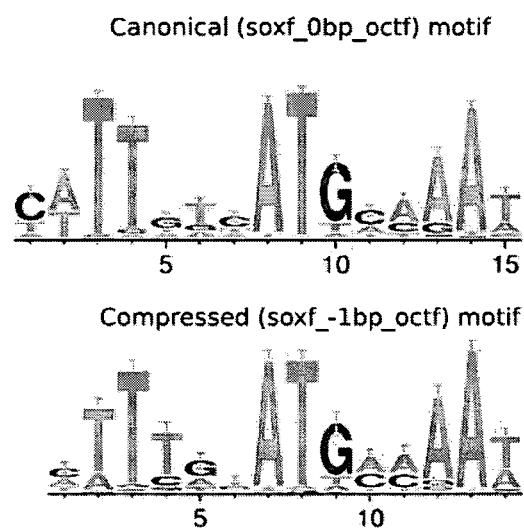

The second most abundant motif detected in the Sox2/Oct4 dataset was a novel 'compressed' motif (here labelled as: soxf_-1bp_octf, FIG. 7C, a 54% increase over background). The compressed motif differs from the canonical motif by deletion of a single nucleotide at position 7 of the canonical sox/oct composite motif that is only weakly specified in the canonical motif (FIG. 7C). The sequences identified by this alternative were recovered, PWM were compressed and weblogo representation of the newly identified compressed motif was generated (FIG. 7C).

Figure 7D:
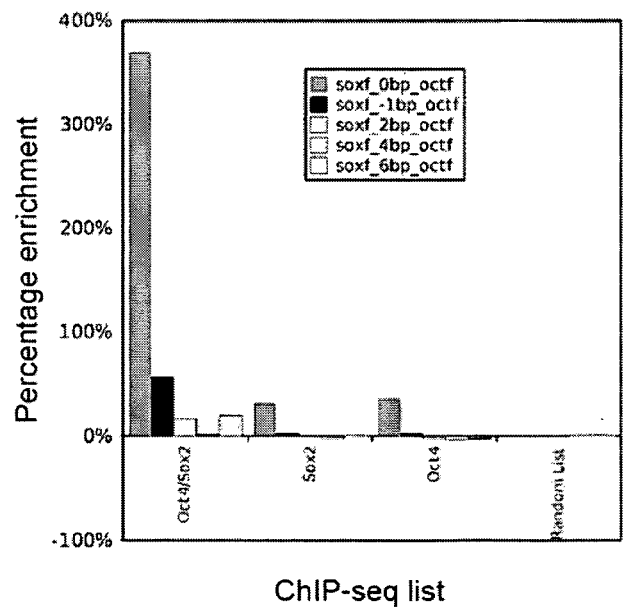

Next the motif frequencies in genomic regions bound by Sox2 or Oct4 alone were compared with regions co-bound by Sox2 and Oct4 (FIG. 7D). As anticipated, canonical and compressed composite motifs were detected less frequently at sites occupied by individual TFs as compared to co-bound sites.

Figure 8A:
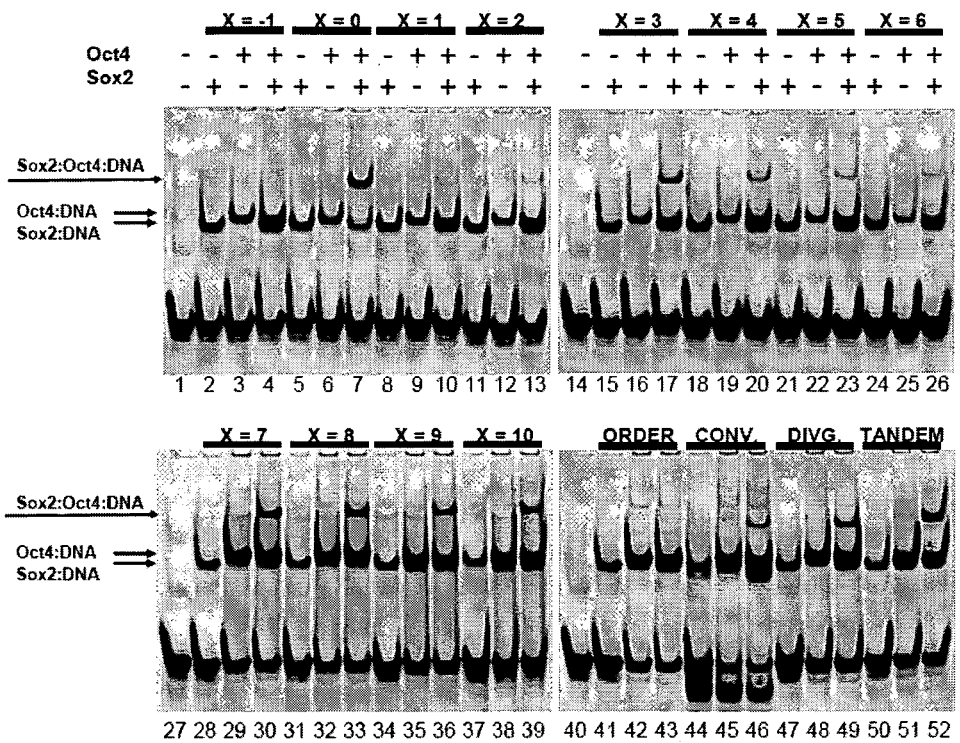
FIG. 8: Differential assembly of Sox2HMG and Oct4POU (A) and Sox17HMG and Oct4 (D) on a series of different motif configurations. The co-occurrence of canonical and compressed motifs within genomic regions co-bound by Sox2 and Oct4 in mouse embryonic stem cells are depicted in (B). The portion of motifs with shared genomic coordinates is shown in (C).

Profiling of Sox/Oct4 Binding to Differentially Configured Motifs: To assess the preference of Sox2 and Oct4 to physically assemble on differentially configured sox/oct motifs in vitro, electrophoretic mobility shift assays (EMSA) were conducted using purified DNA binding domains (DBDs) of Sox2 and Oct4. The heterodimerization potential of Sox2/Oct4 DBD pairs was screened on a panel of systematically modified sox/oct composite motifs (FIG. 7A). A strong cooperative interaction of Sox2 and Oct4 on the canonical element was observed (x=0, FIG. 8A, lanes 5-7). However, the dimerization potential was strongly diminished if a spacer of one or two base pairs was introduced (FIG. 8A, lanes 8-13). Heterodimerization was enabled on elements with a spacer length between 3 and 10 nucleotides, albeit with reduced efficiency as compared to the canonical element, suggesting an additive or weakly competitive binding mode (FIG. 8A, lanes 15-39). If the arrangement of the motifs is altered (FIGS. 7A, 82A, lanes 41-49) dimer formation is abrogated for a changed motif order (octf_0bp_soxf), strongly diminished for the converging motif (soxf_0bp_octr) and reduced for the diverging orientation (soxr_0bp_octf). Unexpectedly, the newly identified compressed motif did not enable heterodimer formation though the individual proteins bound with high affinity (FIG. 8A, lanes 2-4).

Three scenarios could explain the abundance of a compressed motif in genomic regions co-targeted by Sox2 and Oct4 despite the inability of the two proteins to heterodimerize in this sequence context. Firstly, the over-representation of the compressed motif could be caused by independent ChIP enrichment of Sox2 or Oct4 bound singly to this site and the averaging over a large population of cells creates the notion of co-occurrence of both proteins. Secondly, compressed motifs could be located in the proximity to canonical motifs that recruit functional Sox2/Oct4 heterodimers. In the latter scenario compressed motifs would be co-purified in ChIP experiments while the actual binding event occurs at a nearby canonical motif. A third possibility is that the apparent enrichment of the compressed motif is inflated by its similarity to the canonical motif.

Figure 8B:
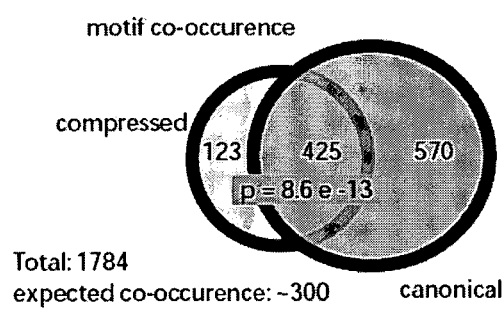
Figure 8C:
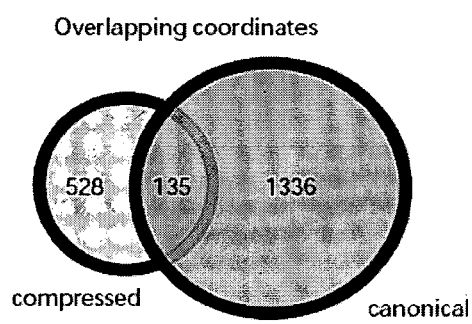

To further explore the last two issues, the relationship between canonical and compressed motifs was examined by measuring the co-occurrences of both motifs in the Sox2/Oct4 bound regions. There are 1784 Sox2/Oct4 bound regions, and the canonical motif is present at least once in 995 of these locations while the compressed motif occurs 548 times. 425 regions contained both a compressed and a canonical motif, which was a statistically significant co-occurrence (p=8.6e-13) (FIG. 8B). To establish that the compressed motif constitutes a genuine motif remote from the canonical version and not a cryptic motif hidden within the canonical motif the precise locations of the motifs in the mouse genome was recovered and the intersection of genomic coordinates was analyzed (FIG. 8C). 135 compressed/canonical motifs were sharing genomic coordinates within 1 bp of each others coordinates centres (including sites on the opposite strand), indicating motif overlap (FIG. 8C). However, the majority of compressed motifs (528) are positionally distinct from the canonical motif suggesting that the compressed motif constitutes a genuine motif variant. To explore the third possibility, it was investigated whether the compressed motif is actually a subset of the canonical motif. Analysis of the pwm's and the sequences that match the pwm was performed and it was found that the vast majority of sequences retrieved by the pwm's for the compressed and canonical motifs are distinct.

Figure 8D:
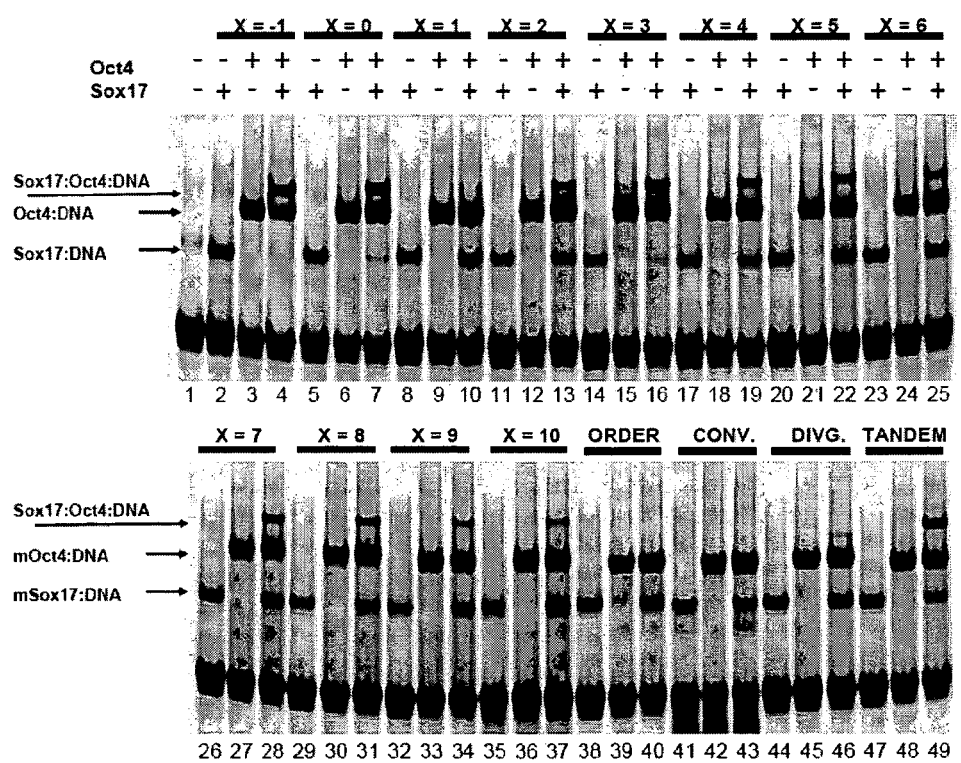

It had been previously shown that the binding affinities of Sox2 and the F group Sox protein Sox17 to sox motifs are indistinguishable (Palasingam, P. et al. *J Mol Biol* (2009) 388: 619-30). To compare the heterodimerization properties of Sox2 and Sox17, the differential assembly of Sox17 and Oct4 DBDs to the same panel of sox/oct motif configurations tested earlier for Sox2 and Oct4 was assessed. The overall pattern of heterodimerization on most motif configurations recapitulates observations made for the Sox2/Oct4 pair (FIG. 8D, lanes 5-49). However, in stark contrast to the inability of Sox2 and Oct4 to co-assemble on the compressed motif, Sox17 and Oct4 exhibited a cooperative binding mode on this element (FIG. 8D, lanes 2-4). This finding indicates a qualitative binding difference of the Sox2/Oct4 versus the Sox17/Oct4 heterodimers on cis-regulatory DNA which might constitute the biochemical basis for their distinct roles in mammalian development.

Figure 9A:
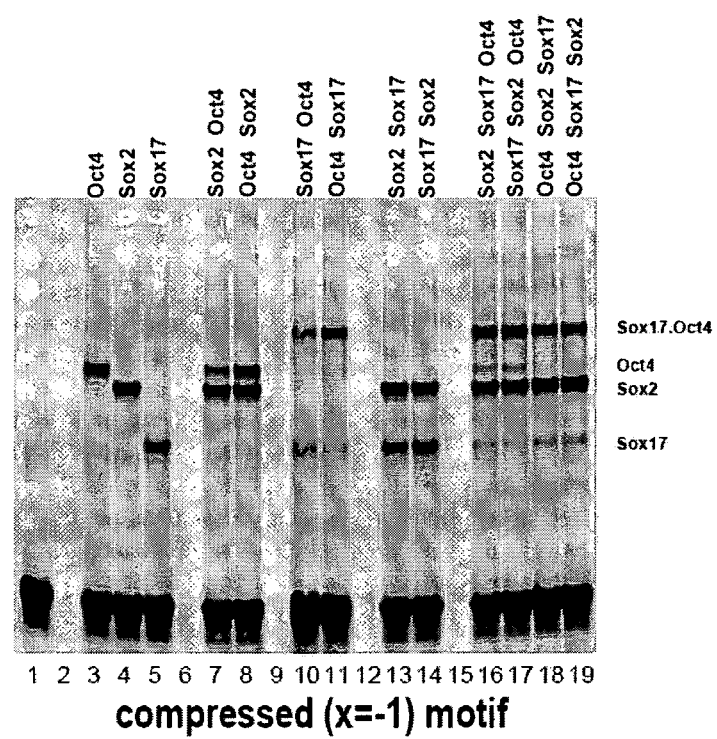
FIG. 9: (A and B) Differential assembly of Sox2/Oct4 and Sox17/Oct4 on the compressed (A) and canonical elements (B). (C) model summarizing the differential assembly of Sox2/Oct4 and Sox17/Oct4 on the canonical versus the compressed element.
Figure 9B:
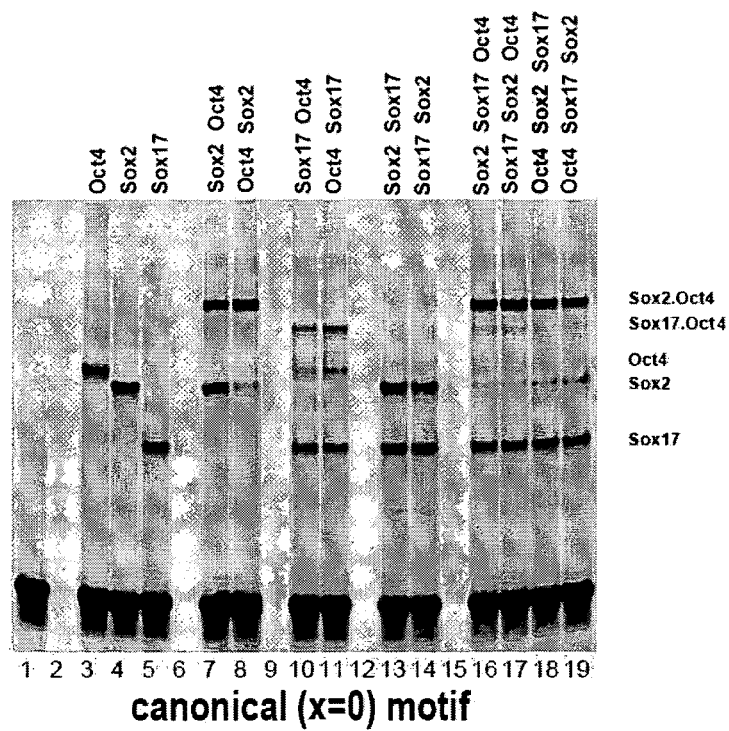
Figure 9C:
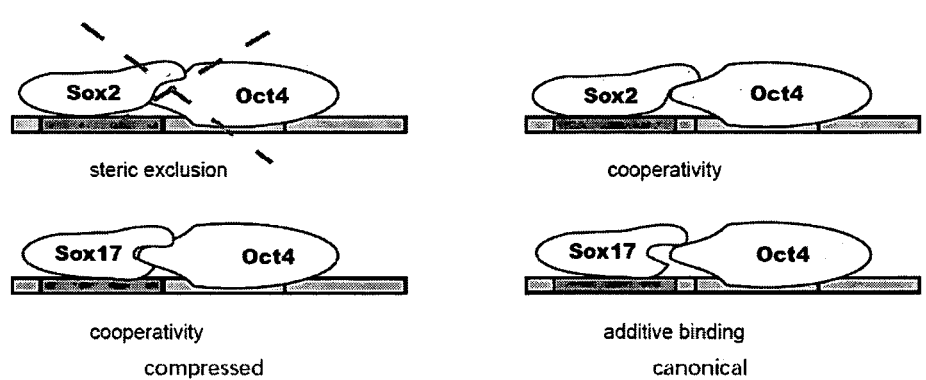

Assembly of Distinct Sox/Oct4 Pairs Depends on the cis-regulatory Context: To further dissect the differential assembly of the Sox2/Oct4 versus Sox17/Oct4 pairs in different cis-regulatory contexts competition binding experiments were conducted on the canonical and the compressed elements. FIG. 9A lanes 3-5 indicate that all binding partners retarded equal amounts of DNA at the experimental condition when added individually. To assess whether the sequence of the addition of the protein components affects the heterodimerization efficiency, the labeled DNA probe was premixed first with either Sox2 or Sox17 or the Oct4 binding partners before adding the remaining proteins to the reaction. Lanes 7-8 and 10-11 confirm that only the Sox17/Oct4 heterodimer was capable of assembling on the compressed sox/oct element whereas the co-binding of Sox2 and Oct4 was obstructed. The heterodimerization of Sox17 and Oct4 on the compressed element was not abrogated in the presence of Sox2 (Lanes 16-19) and the sequence of component addition had only marginal effects on complex formation. A similar experiment was carried out to study the assembly behavior on the canonical sox/oct motif (FIG. 9B). Sox2 and Oct4 exhibited a cooperative binding mode on this element as indicated by a complete supershift of the Oct4/DNA complex if Sox2 was present (Lane 7-8). However, when Sox17 and Oct4 were incubated with the canonical element, the supershift of the Oct4/DNA complex was incomplete, suggesting an additive or only weakly cooperative binding mode. Furthermore, when the three factors were incubated together the majority of supershifted Oct4 migrated in a Sox2/Oct4/DNA complex while the Sox17/Oct4/DNA complex was of markedly lower abundance. The bulk of the Sox17 protein remained singly bound to DNA. The sequence of addition of the Sox proteins did not significantly affect the experimental outcome. These results indicate that Sox2 exhibits biochemical properties at the Oct4 binding interface enabling it to out-compete Sox17 on the canonical sox/oct element. Together, while Sox17/Oct4 binding was sterically possible on the canonical element (Lane 10-11) complex formation was strongly enhanced on the compressed element for the Sox17/Oct4 pair (3A lane 10/11). Conversely, Sox2/Oct4 dimerization was occluded, on the compressed motif presumably due to steric hindrance (FIG. 9C).

A series of control experiments were conducted to establish the significance of these findings and tested another F-group Sox protein, Sox7, a shorter version of the Sox2 protein restricted to the core of the HMG domain and altered the spacer residue of the canonical motif (FIG. 1). In summary, the preference to assemble with Oct4 on compressed elements appears a robust property of the F-group Sox proteins Sox7 and Sox17, whereas Sox2/Oct4 dimerization is impaired on this motif. In addition, the structural elements that equip the Sox proteins under study with the ability to differentially assemble on subtly different motif variants must reside within the core of the HMG domain.

Figure 10A:
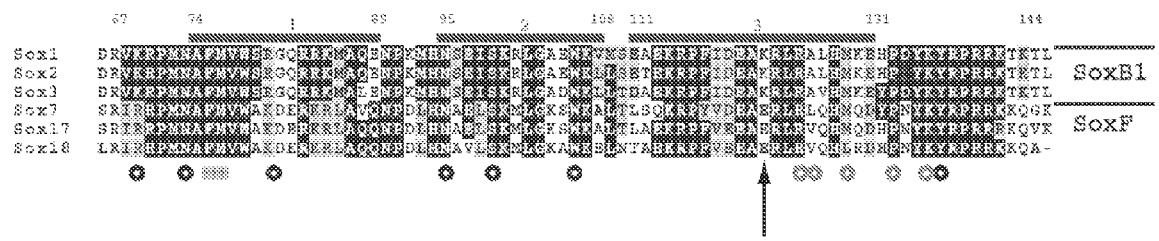
FIG. 10: (A) Alignment of the amino acid sequence of all mouse Sox proteins; Sox1(SEQ ID NO: 48); Sox2 (SEQ ID NO: 49); Sox3 (SEQ ID NO: 50); Sox7 (SEQ ID NO: 51); Sox17(SEQ ID NO: 52); and Sox18 (SEQ ID NO: 53). (B) Structural model prepared using pymol by using the structural coordinates for Sox17 and the Sox2/Oct1 on DNA. (C) Point mutations at the Sox/Oct4 interface swap the differential assembly behavior of Sox2 and Sox17 on the canonical versus the compressed element.
Figure 10B:
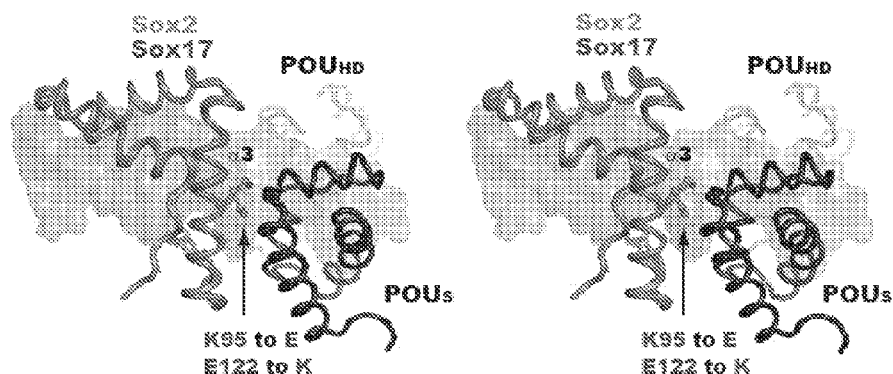
Figure 10C:
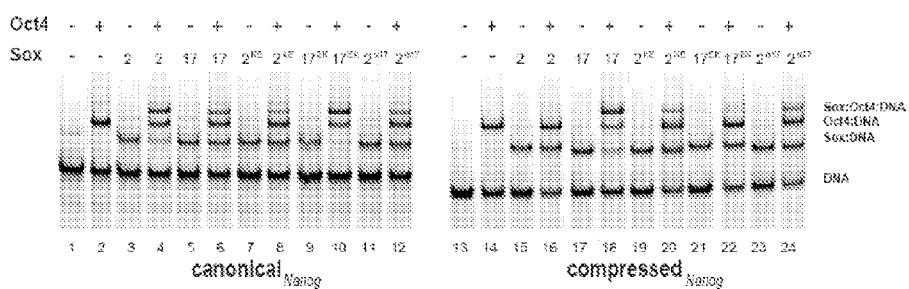

Point Mutations at the Oct4 Interaction Surface Swap the DNA Dependent Dimerization Potential of Sox2 and Sox17: Structural studies on Sox 17 (Palasingam, P. et al. *J Mol Biol* (2009) 388: 619-30) and Sox2 (Remenyi, A., Genes Dev. (2003) 17(16):2048-59; Williams, D.C., *J. Biol. Chem.* (2004) 279(2):1449-57) revealed that DNA base contacts as well as the protein induced deformation of the DNA are virtually identical for both proteins. However, a different electrostatic surface potential was observed in a region centered at helix 3 (Palasingam, P. et al. *J Mol Biol* (2009) 388: 619-30) that constitutes the presumed Oct4 contact interface. Overall, Sox B1 and F group proteins exhibit remarkable sequences conservation but residue 122 (Sox17 numbering) at the Oct4 contact interface exhibit a subgroup specific pattern (FIG. 10A). B group Sox proteins contain a basic lysine at this position which is replaced by an acidic glutamate in F group Sox proteins which appears to alter the electrostatic properties of both proteins (Palasingam, P. et al. *J Mol Biol* (2009) 388: 619-30). To test if this residue causes the differential assembly of Sox2 and Sox17 with Oct4 lysine 95 in Sox2 was mutated into a glutamate (Sox2KE) while glutamate 122 in Sox17 was converted to a lysine (Sox17EK, FIG. 10B). In addition, a Sox2 construct was generated in which all 8 helix-3 residues in proximity to the putative Oct4 contact interface were converted into their corresponding counterparts found in Sox17 (denoted Sox2α17, FIG. 10B). Next the potentials of the mutated Sox proteins for co-assembly with Oct4 on the canonical and compressed elements derived from the regulatory region upstream of Nanog (Rodda, D. J. et al. *J Biol Chem* (2005) 280:24731-7) were assessed. The wildtype Sox2 and Sox17 proteins bind the Nanog promoter derived element identically to the idealized elements described earlier (FIG. 10C, Lanes 3-6; 15-18). Mutation of the Oct4 interface, however, swapped the binding profiles of Sox2 and Sox17. The ability of the mutated Sox2 constructs Sox2KE and Sox2α17 to dimerize with Oct4 on the canonical motif was substantially weakened (compare FIG. 10 lanes 4, 8 and 12). Conversely, the Sox17EK cooperated more strongly with Oct4 than WT Sox17 on the canonical element (lanes 6 and 10). Consistently, testing binding of the mutated Sox constructs to Oct4 on the compressed element displayed the reverse pattern. Mutating the Sox2HMG to Sox2KE installed the ability of this construct to assemble with Oct4 on the compressed element which was denied to the wildtype domain (lanes 16, 20, 24). Conversely, the Sox17EK mutation eliminated a key feature necessary for co-assembling with Oct4 on the compressed element (lanes 18, 22). These results indicate that a single amino acid at the Oct4 contact interface constitutes an important determinant for a qualitative binding difference of the Sox2/Oct4 versus the Sox17/Oct4 transcription factor pairs on motif variants.

Generation of induced pluripotent stem cells using a rationally engineered Sox17 construct: Sox2 and Sox17 differ in their ability to generate iPS cells (Nakagawa, M. et al. *Nat Biotechnol* (2008) 26:01-6). Although Sox2 in combination with Oct4, Klf4 and c-myc can reprogram somatic cells, Sox17 cannot. iPS cell generation was used to assess the capacity of the designed recombinant Sox variants to induce pluripotency.

Figure 11A:
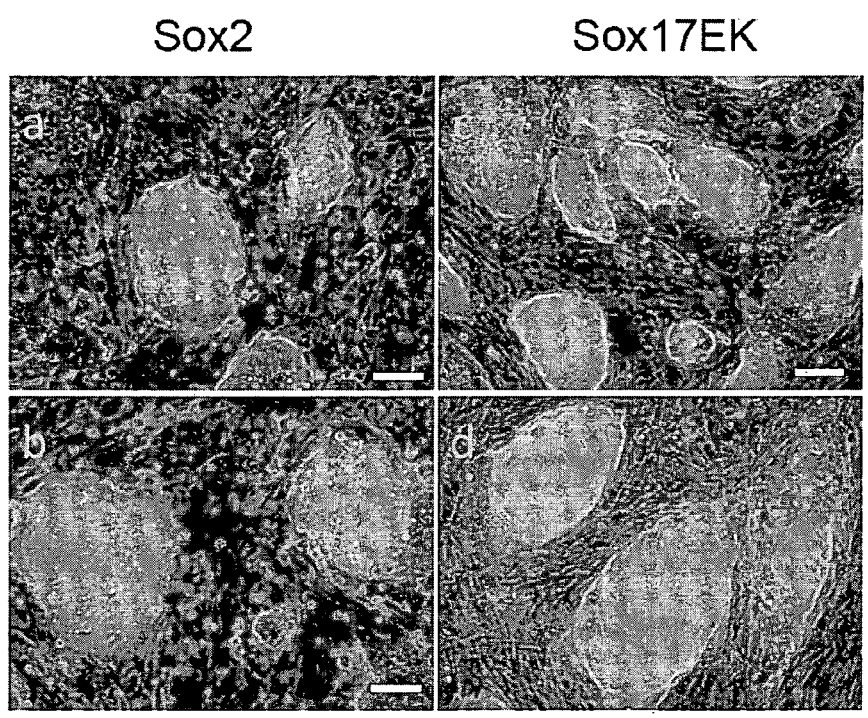
FIG. 11: Characterization of iPS clones reprogrammed by Sox17EK. A. Combined bright field and fluorescent photographs are presented of isolated iPS colonies. B. Q-RT-PCR was performed to determine expression of pluripotency genes by iPS clones reprogrammed by Sox2, Sox17EK, or Sox2KE, as indicated. C. Uniform expression of SSEA-1 and Sox2 on iPS clones.

Four co-transfected transcription factors are required to generate mouse iPS cells Oct4, c-Myc, Klf4, (OCK) and Sox2 (Takahashi and Yamanaka (2006) *Cell* 126:663-676). In the reprogramming assay, an average of 68 iPS clones were generated with OCK plus Sox2 and no colonies appeared when Sox2 was omitted (Table 2). OCK plus Sox17 did not generate any iPS colonies as previously described (Nakagawa, M. et al. *Nat Biotechnol* (2008) 26:01-6). It was next confirmed that Sox17EK could replace Sox2 in the generation of iPS cells (FIG. 11A and Table 2). In three independent experiments, an average of 295 iPS colonies were generated per plate of MEFs. The morphology of the colonies and level of Oct4-GFP expression in the reprogrammed cells by Sox17EK were indistinguishable from those generated by Sox2 (FIG. 11A).

The numbers of iPS colonies generated by wildtype and mutant version of Sox2 and Sox17 in 3 separate experiments (Exp. A, B, and C) are shown in Table 2. The indicated versions of the Sox factors were cotransduced by retroviral vectors together with Oct4, c-myc, and Klf4 (OCK) into MEF cells. Oct4-GFP+ colonies appearing on each plate, performed in triplicate (average±S.D.), were counted 3 weeks post infection: The overall average (Avg.) number of colonies generated in the three experiments is shown in the last column.

TABLE 2

Summary of iPS colonies derived from alternative forms of Sox

| Sox factor | Number of iPS Colonies | | | |
|---|---|---|---|---|
| | Exp. A | Exp. B | Exp. C | Avg. |
| Sox2 | 57 ± 19 | 56 ± 19 | 90 ± 19 | 68 |
| Sox17 | 0 | 0 | 0 | 0 |
| Sox17EK | 312 ± 124 | 164 ± 124 | 410 ± 124 | 295 |
| Sox2KE | 56 ± 24 | 75 ± 24 | 104 ± 24 | 78 |
| Sox2α17 | 0 | 0 | 0 | 0 |
| OCK only | 0 | 0 | 0 | 0 |

Figure 11B:
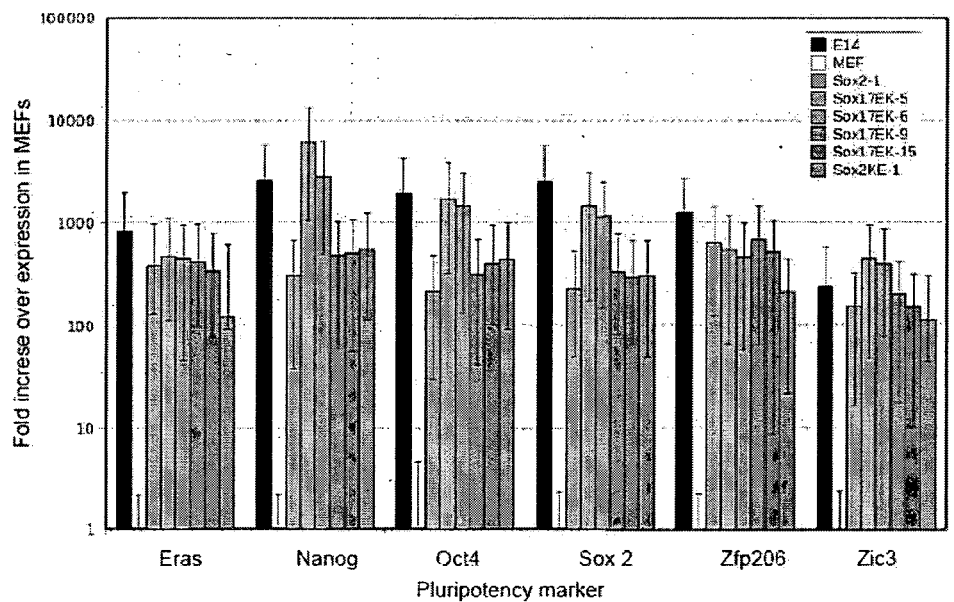
Figure 11C:
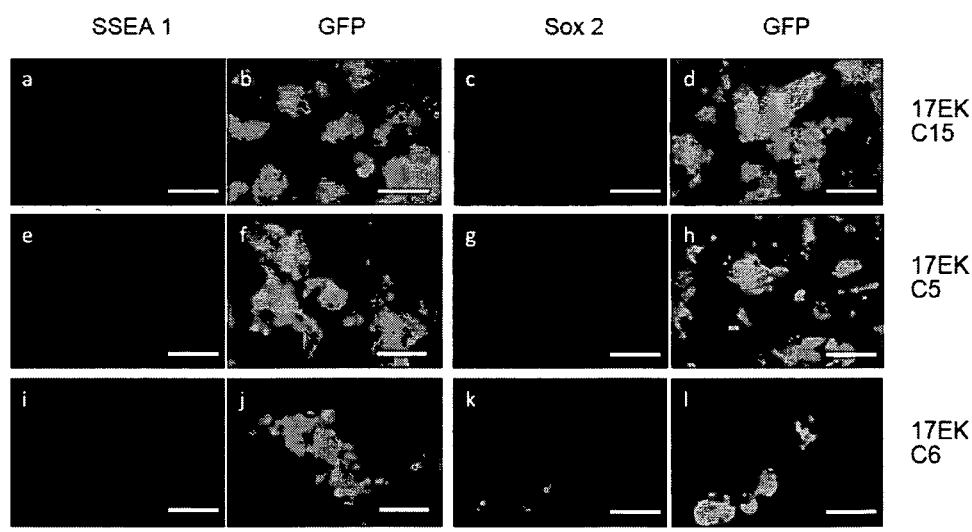

To confirm that the iPS cells generated by Sox17EK were bonafide iPS cells, a screen was performed for a set of markers expressed in reprogrammed, pluripotent cells, but are not found in MEFs. Several of the iPS colonies generated were expanded and the gene expression of a selection of marker genes was measured by quantitative RT-PCR (FIG. 11B). All of the pluripotency markers Eras, Nanog, Oct4, Sox2, Zfp206 and Zic3, exhibited comparable levels to normal ES cells and OCK Sox2 iPS cells while the original MEFs had low expression (FIG. 11B).We also immunostained three of the Sox17EK iPS lines for Sox2 and the pluripotency marker SSEA-1 (FIG. 11C). All Sox17EK iPS clones examined uniformly expressed the cell surface marker SSEA-1 and the nuclear localized transcription factor, Sox2. We also confirmed transfection of the transgene's insert size and nucleotide sequence from iPS Clones (FIG. 2). Collectively, these data demonstrate that Sox17EK, in cooperation with OCK, induces pluripotency.

The biochemical data indicate that the Sox2KE and Sox2a17 mutants weaken the heterodimerization potential of Sox2 with Oct4 on canonical elements similarly to that observed for Sox17. Sox2KE was tested in combination with OCK; it was found that Sox2KE retained the wildtype Sox2 activity as it was able to generate iPS cells (Table 2). However, the Sox2α17 with additional mutations at the Oct4 contact interface were unable to induce pluripotency in the same assay (Table 2 and FIG. 11). One interpretation of these results is that the Sox2α17 interferes with Oct4 interactions more strongly than Sox2KE in an in vivo setting relative to in vitro measurements. Alternatively, it cannot be excluded that there is no simplistic one-to-one relationship between the potential to heterodimerize with Oct4 on canonical elements in vitro and the iPS inducing properties. If so, interactions with third factors, sub cellular localization, protein stability and post-translational modifications are amongst the candidate processes that could be differentially affected in the Sox2KE versus the Sox2α17 mutants.

This study involved in silico identification of a novel compressed motif, the biochemical demonstration that this DNA motif can recruit different Sox/Oct pairs in contrast to its canonical counterpart, and the reverse engineering of the differential assembly behavior by analyzing structural models. Ultimately, it was demonstrated that a single point mutation introduced at a site that drastically affects Oct4 interaction in vitro is sufficient to turn Sox17 into an iPS reprogramming factor.

Example 2

Figure 12A:
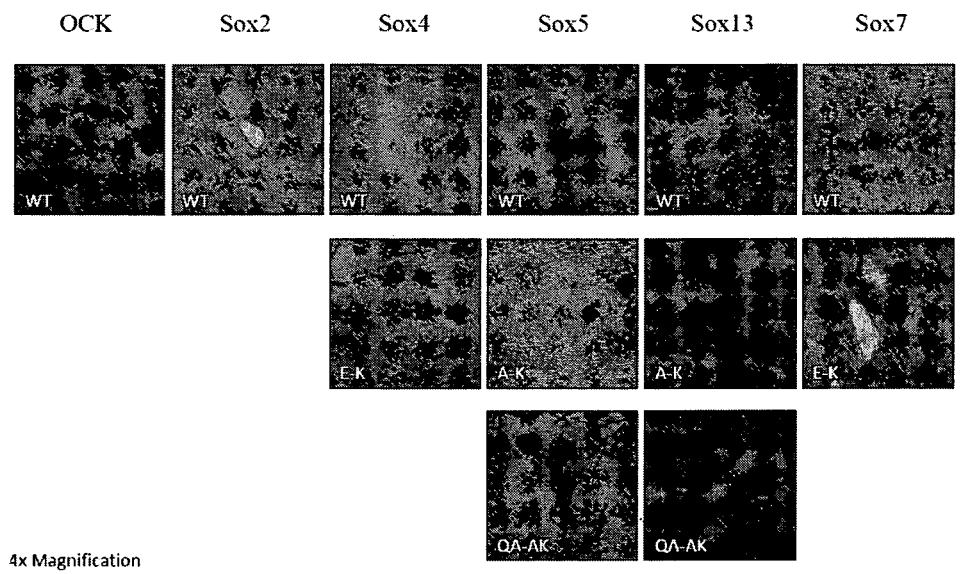
FIG. 12: Results of induced pluripotency using OCK alone or with Sox2 or mutants of Sox4, Sox5, Sox13 or Sox7.
Figure 12B:
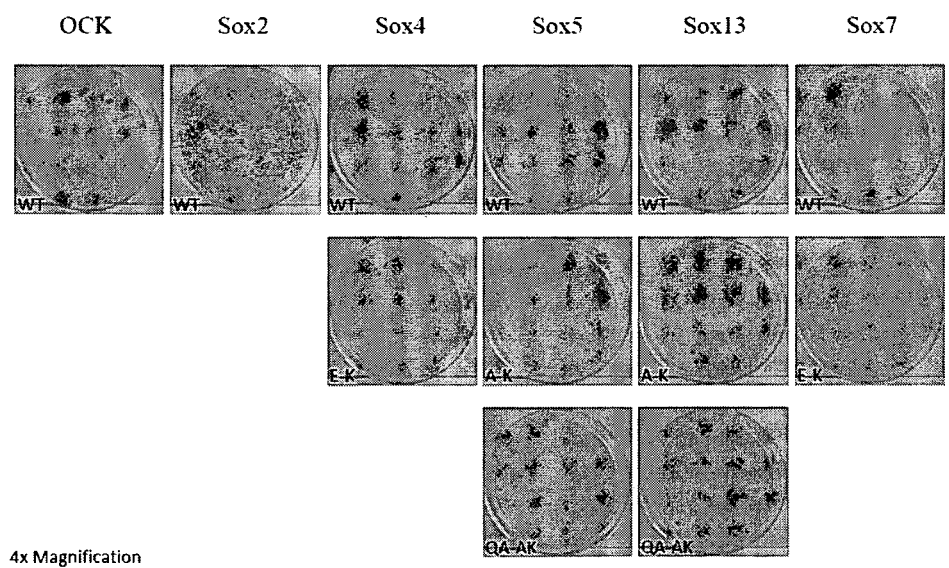
Figure 13:
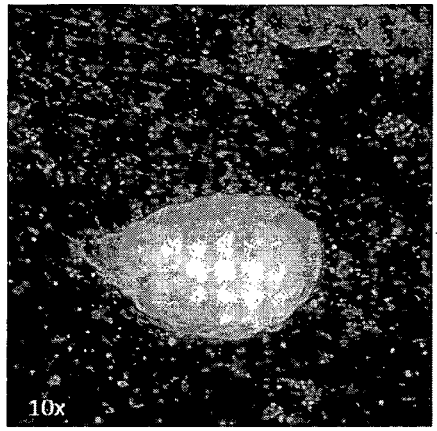
FIG. 13: Pluripotent colonies induced by Sox7EK.
Figure 13:
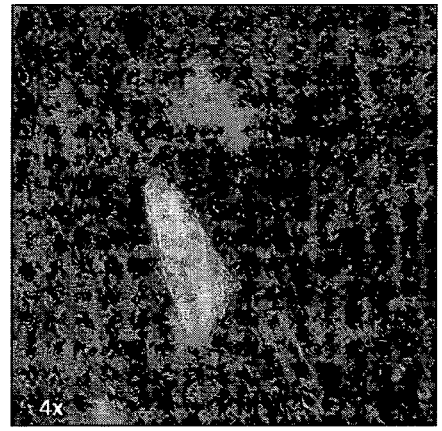
Figure 14A:
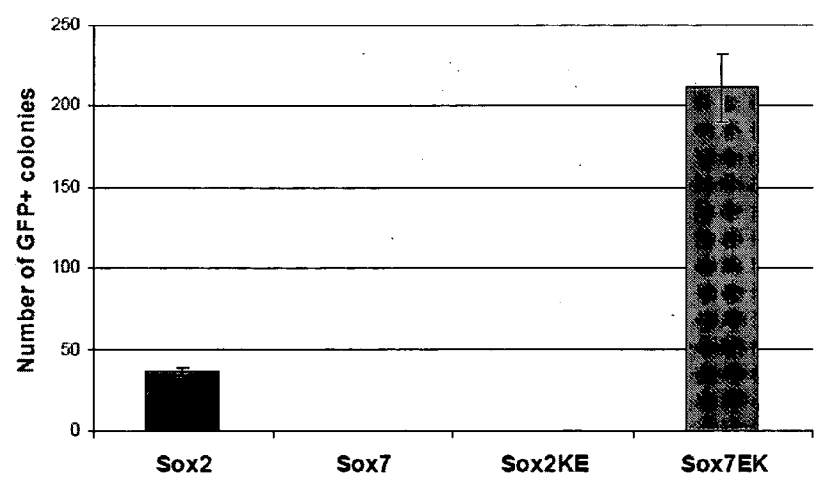
FIG. 14: Efficiency of induction of pluripotency.
Figure 14B:
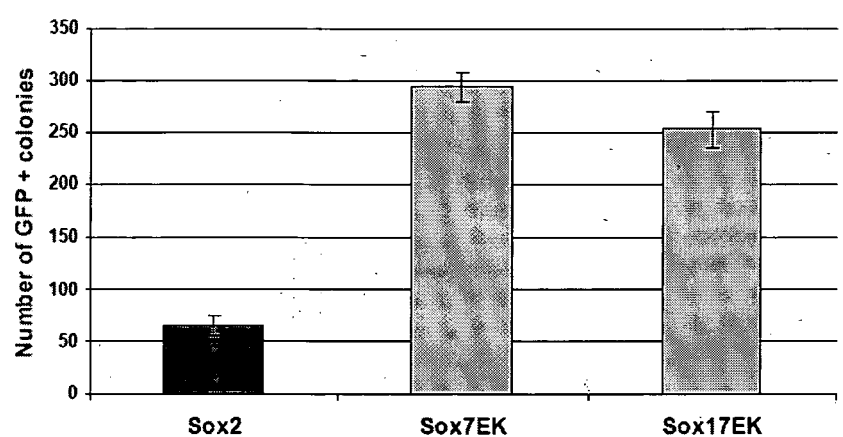

Sox7 was mutated at the corresponding Glu residue in a similar fashion to Sox17 as described in Example 1 to produce a Sox7EK mutant. Sox7EK was able to induce pluripotency, in contrast to analogous mutant forms of Sox4, Sox5 and Sox13 (FIG. 12A, 12B). Colonies were visible at least as early as day 14 (FIG. 13). As with Sox17, wildtype Sox7 did not induce pluripotent colonies, but Sox7EK was more efficient than Sox2 (wildtype) at producing pluripotent colonies (FIG. 14A, 14B).

FIG. 12: Results of induced pluripotency using OCK alone or with Sox2 or mutants of Sox4, Sox5, Sox13 or Sox7. A. GFP fluroescence. B. Alkaline phosphatase staining.

FIG. 13: Pluripotent colonies induced by Sox7EK. Colonies were visible as early as day 14.

FIG. 14: Efficiency of induction of pluripotency. A. Wild-type Sox2 and Sox7EK were able to induce pluripotency whereas Sox2KE and Sox7 wildtype did not. B. As with Sox17EK, Sox7EK is more efficient at inducing pluripotency when compared to Sox2.

In an extension of the previous work where it was shown that Sox17EK mutant can give higher iPS production when replacing Sox2 (the Yamanaka factor) used with the other 3 factors (Oct4,Klf4,cMyc), it was shown that Sox7EK mutant works as well as Sox17EK in forming iPS colonies, both of which mutants are at least 4× more efficient than Sox2.

Figure 16:
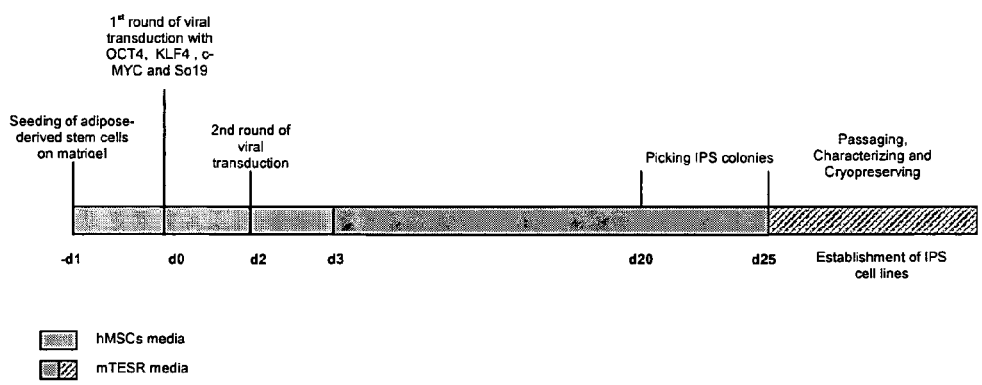
FIG. 16: An overview of the generation of human iPS cells using human adipose-tissue derived MSCs.

As well, experiments indicated that it is the C terminal "activation" domain of Sox17 which gives the higher efficiency of iPS generation. A chimera consisting of Sox2HMG domain (amino acids 1 to 121) with the Sox17 C-terminal activation domain (amino acids 147 to 420) showed the increased efficiency (FIG. 16).

Figure 15A:
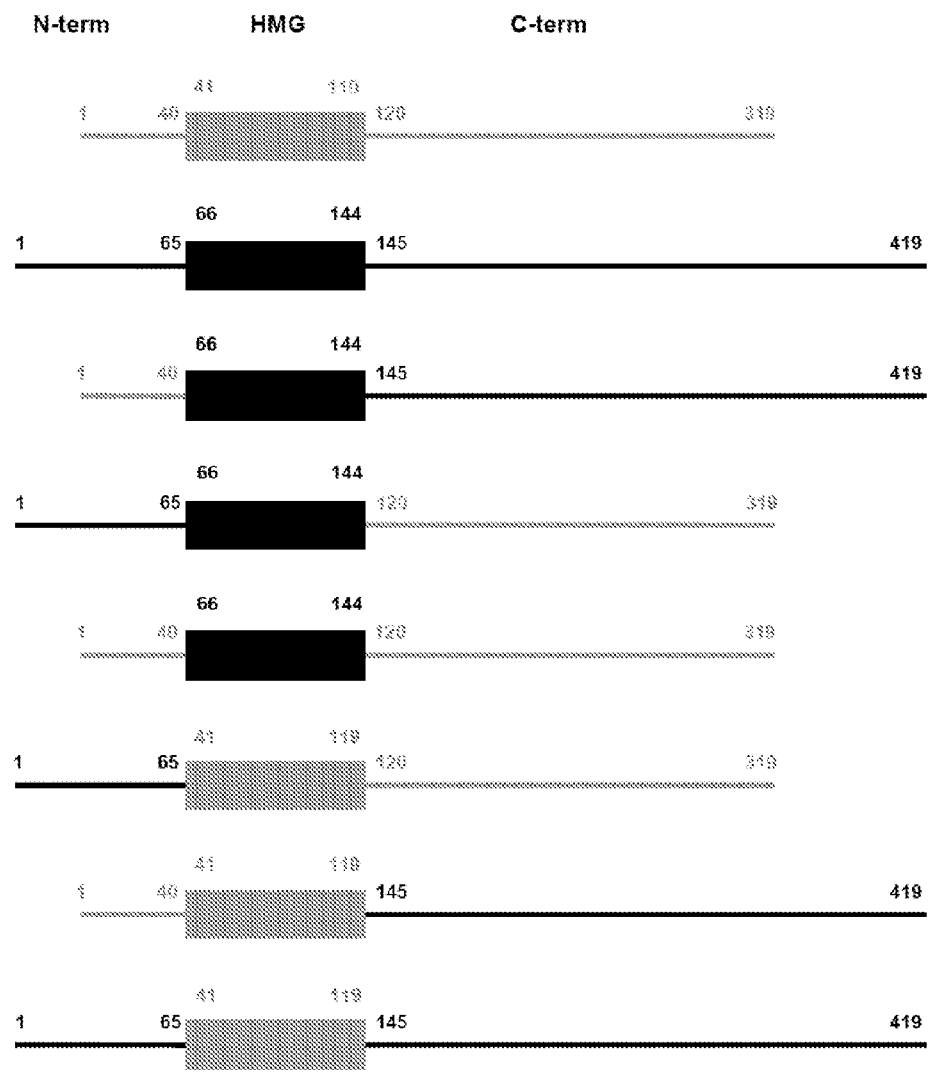
FIG. 15: Chimeric Sox2 and Sox17 proteins and induction of pluripotency.
Figure 15B:
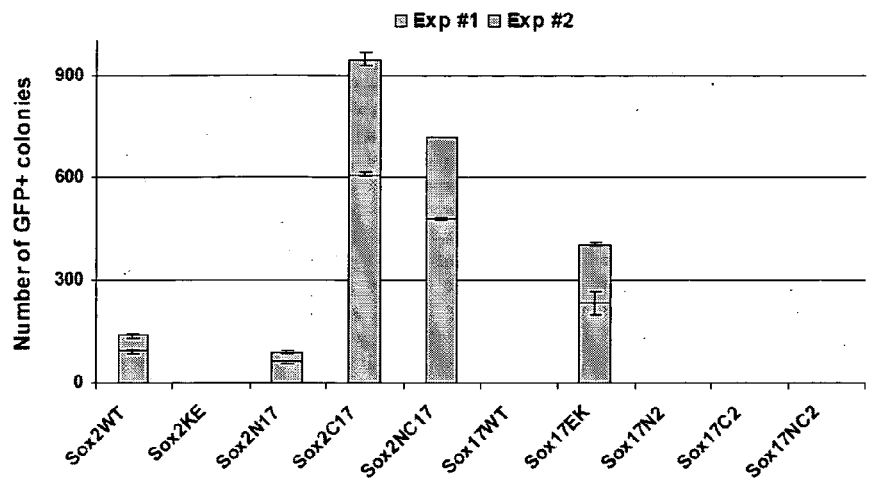

FIG. 15: Chimeric Sox2 and Sox17 proteins and induction of pluripotency. A. Constructs of Sox2 and Sox17. B. Pluripotent colonies induced using the various chimeric Sox protein constructs.

Example 3

There is a high homology between human and mouse transcription factors. The HMG domain is 100% conserved between the two species.

Human induced pluripotent stem (iPS) cells can be generated by viral transduction of human adipose-tissue derived mesenchymal stem cells (hAd-MSCs) (Sun, N. et al., *Proc Natl Acad Sci USA* (2009) 106:15720-725) with the four "Yamanaka factors": OCT4, SOX2, KLF4 and c-MYC (Takahashi and Yamanaka (2006) Cell 126:663-676). The detailed protocol is as follows.

For virus production, pMXs retroviral vectors are used in which the cDNA sequences of Oct4, c-Myc, Klf4, Sox2, Sox2KE, Sox7, Sox7EK, Sox17 and Sox17EK were cloned. 20×10$^6$ of virus-producing 293GP2 cells are plated in a 15 cm dish and transfected the next day by using Fugene6 transfection reagent. 112.5 μl of Fugene are mixed with 750 μl of DMEM for 5 minutes. Then 22.5 μg of pMXs vector and 22.5 μg of a VSV-G vector are added drop by drop. 15 minutes later the mix is transferred onto the 293GP2 cells and incubated overnight. The next day (FIG. 16, d-1) the media of 293GP2 cells is changed with 20 ml of fresh media, and 380 000 cells hAd-MSCs are plated in 3 different 6 cm dishes coated with human ES-qualified matrigel (BD Biosciences) in standard hAd-MSCs media. The day after the virus is collected and concentrated by using Amicon® Ultra Centrifugal Filter Units according to the manufacturer's instructions (Millipore) and cells are infected a 1$^{st}$ round with Oct4, c-Myc, Klf4 and the corresponding Sox factor. 20 ml of fresh media is added again in the 293GP2 cells for a second round of infection the next day. The following day the hAd-MSCs media is changed to hES media : mTESR1 media from Stem Cell Technologies. The media is then changed every consecutive day from 20 to 25 days till the appearance of hES-like colonies. Then the colonies are stained alive for the pluripotency marker SSEA4 and counted under a fluorescent microscope. Positive colonies are then picked in 24 well format plates for individual amplification and more characterization. Results are shown in FIG. 17.

FIG. 16: An overview of the generation of human iPS cells using human adipose-tissue derived MSCs.

Figure 17:
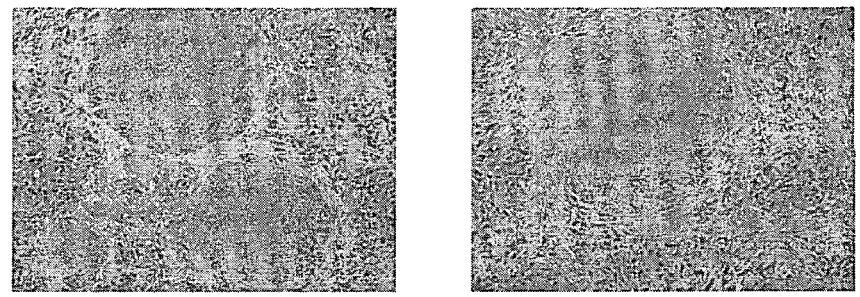
FIG. 17: Human iPS colonies induced using Oct4+c-Myc+Klf4+Sox17EK.

FIG. 17: Human iPS colonies induced using Oct4+c-Myc+Klf4+Sox17EK.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs.

All lists or ranges provided herein are intended to include any sub-list or narrower range falling within the recited list or range.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

Ben-Gal I, Shani A, Gohr A, Grau J, Arviv S, Shmilovici A, Posch S, Grosse I (2005). Identification of Transcription Factor Binding Sites with Variable-order Bayesian Networks. Bioinformatics 21, 2657-2666.

Chen X, Xu H, Yuan P, Fang F, Huss M, Vega VB, Wong E, Orlov YL, Zhang W, Jiang J, Loh YH, Yeo HC, Yeo ZX, Narang V, Govindarajan KR, Leong B, Shahab A, Ruan Y, Bourque G, Sung WK, Clarke ND, Wei CL, Ng HH. Integration of external signaling pathways with the core transcriptional network in embryonic stem cells. Cell. 2008 Jun 13;133(6):1106-17.

Takahashi, K., and Yamanaka, S. (2006). Induction of pluripotent stem cells from mouse embryonic and adult fibroblast cultures by defined factors. Cell 126, 663-676.

Van Loo P and Marynen P, (2009) Computational methods for the detection of cis-regulatory modules. Briefings in Bioinformatics, 10, 509-524.

Segal, E. & Widom J. What controls nucleosome positions? Trends Genet. 2009 Aug;25(8):335-43.

Boyer, L. A. et al., Core transcriptional regulatory circuitry in human embryonic stem cells, Cell 122, 947-52 (2005).

Loh, Y. H. et al., The Oct4 and Nanog transcription network regulates pluripotency in mouse embryonic stem cells. Nat. Genetics 38, 431-40 (2006).

Bowles, J., Schepers, G. & Koopman, P. Phylogeny of the Sox family of developmental transcription factors based on sequence and structural indicators. Dev. Biol. 227, 239-55 (2000).

Ryan, A. K. & Rosenfield, M. G. POU domain family values: flexibility, partnerships, and developmental codes. Genes & Dev. 11, 1207-25 (1997).

Wegner, M. From head to toes: the multiple facets of Sox proteins. Nucleic Acid Res 27, 1409-20 (1999).

Badis, G. et al. Diversity and complexity in DNA recognition by transcription factors Science (2009) 324(5935):1720-3.

Rodda, D. J. et al. Transcriptonal regulation of nanog by OCT4 and SOX2. J Biol Chem 280, 24731-7 (2005).

Tanaka, S. et al. Interplay of SOX and POU factors in regulation of the Nestin gene in neural primordial cells. Mol Cell Biol 24, 8834-46 (2004).

Kuhlbrodt, K. et al. Cooperative function of POU proteins and SOX proteins in glial cells. J Biol Chem 273, 16050-7 (1998).

Stefanovic, S. et al. Interplay of Oct4 with Sox2 and Sox17 : a molecular switch from stem cell pluripotency to specifying a cardiac fate. J Cell Biol 186, 665-73 (2009).

Palasingam, P., Jauch, R., Ng, C. K. & Kolaktar, P. R. The structure of Sox17 bound to DNA reveals a conserved bending topology but selective protein interaction platforms. J Mol Biol 388, 619-30 (2009).

Avilion, A. A. et al. Multipotent cell lineages in early mouse development depend on SOX2 function. Genes Dev 17, 126-40 (2003)

Zappone, M. V. et al. Sox2 regulatory sequences direct expression of a b-geo transgene to telencephalic neural stem cells and precursors of the mouse embryo, revealing regionalization of gene expression in CNS stem cells. Development 127, 2367-82 (2000).

Que, J. Multiple roles for Sox2 in the developing and adult mouse trachea. Development 136, 1899-1907 (2009).

Que, J. Multiple dose-dependent roles for Sox2 in the patterning and differentiation of anterior foregut endoderm. Development 134, 2521-31 (2007).

Okubo T. Sox2 is required for development of taste bud sensory cells. Genes Dev 20, 2654-59 (2006).

Kanai-Azuma, M. et al. Depletion of definitive gut endoderm in Sox17-null mutant mice. Development 129, 2367-79 (2002).

Seguin C. A., Draper, J. S., Nagy, A. & Rossant, J. Establishment of endoderm progenitors by SOX transcription factor expression in human embryonic stem cells. Cell Stem Cell 3, 182-95 (2008).

Shimoda M, Kanai-Azuma M, Hara K, Miyazaki S, Kanai Y, Monden M, Miyazaki J. Sox17 plays a substantial role in late-stage differentiation of the extraembryonic endoderm in vitro. J Cell Sci. 2007 Nov 1;120(Pt 21):3859-69.

Nakagawa, m. Et al. Generation of induced pluripotent stem cells without myc from mouse and human fibroblasts. Nat Biotechnol 26, 101-6 (2008).

Nichols, J. et al. Formation of pluripotent stem cells in the mammalian embryo depends on the POU transcription factor Oct4. Cell 95, 379-91 (1998).

Reim, G., Mizoguchi, T., Stainier, D.Y., Kikuchi, Y. & Brand, M. The POU domain protein spg (pou2/Oct4) is essential for endoderm formation in cooperation with the HMG domain protein casanova. Dev Cell 6, 91-101 (2004).

Jauch R, Ng C K, Saikatendu K S, Stevens R C, Kolatkar P R. Crystal structure and DNA binding of the homeodomain of the stem cell transcription factor Nanog. J Mol Biol. 2008 Feb 22;376(3):758-70.

Sun N. et al. Feeder-free derivation of induced pluripotent stem cells from adult human adipose stem cells. Proc Natl Acad Sci USA 106, 15720-725 (2009).

Remenyi A, Lips K, Nissen L J, Reinbold R, Schöler HR, Wilmanns M. Crystal structure of a POU/HMG/DNA ternary complex suggests differential assembly of Oct4 and Sox2 on two enhancers. Genes Dev. 2003 August 15;17(16):2048-59.

Williams, D. C. Jr, Cai, M., Clore, G. M. Molecular basis for synergistic transcriptional activation by Oct1 and Sox2 revealed from the solution structure of the 42-kDa Oct1.Sox2.Hoxb1-DNA ternary transcription factor complex. J Biol Chem. 2004 January 9;279(2):1449-57.

What is claimed is:

1. A recombinant mutant Sox17 protein comprising an E to K mutation in the amino acid sequence LAEKRPFVEEAER-LRVQHMQD of a Sox17 protein, said amino acid sequence corresponding to SEQ ID NO: 37, the mutation occurring at the position corresponding to residue 12 of SEQ ID NO: 37, the recombinant mutant Sox17 protein being capable of inducing conversion of a non-pluripotent cell to a pluripotent cell when present in the non-pluripotent cell in combination with Oct4 and at least one of c-Myc and Klf4.

2. The recombinant mutant Sox17 protein of claim 1, wherein said amino acid sequence corresponding to SEQ ID No: 37 is present in the Sox17 protein set forth in the amino acid sequence of SEQ ID NO: 43 and said mutation occurs at the position corresponding to residue 122 of SEQ ID NO: 43.

3. A recombinant nucleic acid molecule encoding the recombinant mutant Sox17 protein of claim 1.

4. A cell expressing the recombinant mutant Sox17 protein of claim 1.

5. A cell comprising the nucleic acid molecule of claim 3.

6. A method of inducing conversion of a non-pluripotent cell to a pluripotent cell, the method comprising culturing the non-pluripotent cell, into which has been introduced i) the recombinant mutant Sox17 protein of claim 1; ii) Oct4; and iii) at least one of c-Myc and Klf4, in conditions suitable for growth of embryonic stem cells for a suitable amount of time to convert the non-pluripotent cell into a pluripotent cell.

7. The method of claim 6, wherein the recombinant mutant Sox17 protein, Oct4 and at least one of c-Myc and Klf4 have been introduced into the non-pluripotent cell by co-expressing in the non-pluripotent cell the mutant Sox17 protein, Oct4 and at least one of c-Myc and Klf4 from one or more expression vectors.

8. The method of claim 6 wherein the non-pluripotent cell is a fibroblast or a mesenchymal stem cell.

9. The recombinant mutant Sox17 protein of claim 1, wherein said amino acid sequence corresponding to SEQ ID NO:37 is present in the Sox17 protein set forth in the amino acid sequence of SEQ ID NO: 42 and said mutation occurs at the position corresponding to residue 122 of SEQ ID NO: 42.

10. The recombinant nucleic acid molecule of claim 3, wherein the recombinant nucleic acid molecule is present in a retroviral vector.

* * * * *

UNITED STATES PATENT AND TRADEMARK OFFICE
CERTIFICATE OF CORRECTION

PATENT NO. : 8,907,055 B2
APPLICATION NO. : 13/505369
DATED : December 9, 2014
INVENTOR(S) : Prasanna R. Kolatkar et al.

It is certified that error appears in the above-identified patent and that said Letters Patent is hereby corrected as shown below:

In the specification,

Column 8, lines 46 and 48, "Sox 7" should read -- Sox 17 --

Column 14, line 8, "PIVMs" should read -- PWMs --

Column 19, line 52, "The position" should read -- The positions --

Signed and Sealed this
Twenty-seventh Day of October, 2015

Michelle K. Lee
*Director of the United States Patent and Trademark Office*